US012559713B2

(12) United States Patent
Dehottay et al.

(10) Patent No.: US 12,559,713 B2
(45) Date of Patent: Feb. 24, 2026

(54) FERMENTATION PROCESS

(71) Applicant: GlaxoSmithKline Biologicals SA, Rixensart (BE)

(72) Inventors: Philippe Dehottay, Rixensart (BE); Romain Kocks, Rixensart (BE); Quentin Zune, Rixensart (BE)

(73) Assignee: GlaxoSmithKline Biologicals SA, Rixensart (BE)

( * ) Notice: Subject to any disclaimer, the term of this patent is extended or adjusted under 35 U.S.C. 154(b) by 372 days.

(21) Appl. No.: 17/432,671

(22) PCT Filed: Feb. 20, 2020

(86) PCT No.: PCT/EP2020/054426
§ 371 (c)(1),
(2) Date: Aug. 20, 2021

(87) PCT Pub. No.: WO2020/169703
PCT Pub. Date: Aug. 27, 2020

(65) Prior Publication Data
US 2022/0169973 A1 Jun. 2, 2022

(30) Foreign Application Priority Data
Feb. 22, 2019 (EP) .................................... 19158847

(51) Int. Cl.
| | |
|---|---|
| *C12N 1/20* | (2006.01) |
| *A61K 39/02* | (2006.01) |
| *C07K 14/235* | (2006.01) |
| *C12N 9/10* | (2006.01) |

(52) U.S. Cl.
CPC .............. *C12N 1/20* (2013.01); *A61K 39/099* (2013.01); *C07K 14/235* (2013.01); *C12N 9/1077* (2013.01)

(58) Field of Classification Search
CPC ...... C12N 1/20; C12N 9/1077; C07K 14/195; C07K 14/235; A61K 39/099
See application file for complete search history.

(56) References Cited

U.S. PATENT DOCUMENTS

| | | | | |
|---|---|---|---|---|
| 2008/0193475 | A1* | 8/2008 | Dehottay | ................ A61P 31/04 435/246 |
| 2015/0010948 | A1* | 1/2015 | Dehottay | ................. C12N 1/38 435/71.2 |
| 2022/0169973 | A1* | 6/2022 | Dehottay | ............. A61K 39/099 |

FOREIGN PATENT DOCUMENTS

| | | |
|---|---|---|
| EP | 0.387 065 A2 | 9/1990 |
| EP | 0764215 B1 * | 3/1997 |
| JP | 61-285928 A | 12/1986 |
| JP | 3-272681 A | 12/1991 |
| JP | H05304952 A | 11/1993 |

(Continued)

OTHER PUBLICATIONS

Rappouli et al. "Progress towards the development of new vaccines against whooping cough", 1992, Vaccine, vol. 10, Issue 14, pp. 1027-1032. (Year: 1992).*

(Continued)

*Primary Examiner* — Gary B Nickol
*Assistant Examiner* — Amelia Nicole Dickens

(57) ABSTRACT

The present invention relates to processes for *Bordetella* fermentation and virulence factor production, especially PT production, for large scale manufacturing. More particularly, processes including a medium conditioning step carried out prior to inoculation.

15 Claims, 10 Drawing Sheets

(56)                    References Cited

FOREIGN PATENT DOCUMENTS

| JP | 2015057951 | A | 3/2015 |
|----|----|----|----|
| WO | WO 95/33849 | A1 | 12/1995 |
| WO | WO 96/40238 | A1 | 12/1996 |
| WO | WO-2004090140 | A2 | 10/2004 |
| WO | WO 2013/113729 | A1 | 8/2013 |

OTHER PUBLICATIONS

Seubert A., et al., "Genetically Detoxified Pertussis Toxin (PT-9K/129G): Implications for Immunization and Vaccines," Expert Review of Vaccines, Oct. 4, 2014, vol. 13, No. 10, pp. 1191-1204. (Year: 2014).*

International Search Report (PCT/ISA/210) issued in PCT/EP2020/054426, dated May 7, 2020.

Written Opinion of the International Searching Authority (PCT/ISA/237) issued in PCT/EP2020/054426, dated May 7, 2020.

International Prelminary Report on Patentability and Written Opinion (Forms PCT/IB/326, PCT/IB/373, and PCT/ISA/237) for International Application No. PCT/EP2020/054426, dated Sep. 2, 2021.

Bernard K., "The Genus *Corynebacterium* and Other Medically Relevant Coryneform-like Bacteria," Journal of Clinical Microbiology, Oct. 2012, vol. 50(10), pp. 3152-3158.

Doern G V., "Detection of Selected Fastidious Bacteria," Clinical Infectious Diseases, Jan. 2000, vol. 30(1), pp. 166-173.

Rowatt E., "The Growth of Bordetella Pertussis: a Review," Journal of General Microbiology, Oct. 1957, vol. 17(2), pp. 297-326.

Seubert A., et al., "Genetically Detoxified Pertussis Toxin (PT-9K/129G): Implications for Immunization and Vaccines," Expert Review of Vaccines, Oct. 4, 2014, vol. 13, No. 10, pp. 1191-1204.

Quintana-Vazquez D., et al., "Assessment of the Bordetella Pertussis BpCNIC0311 Strain As a Producing Strain of Genetically Detoxified Toxoid (PTg), Filamentous Hemagglutinin (FHA) and Type 2 Pertactin (Prn2)," Journal of Infectious Diseases and Therapeutics, Mar. 2015, vol. 3, pp. 8-20(13 Pages).

Zavatti V., "Application of Flow Cytometry and Fluorescence Spectroscopy to Monitor and Predict the Fermentation Activity in a Vaccine Manufacturing Process," A thesis presented to the University of Waterloo in fulfillment of the thesis requirement for the degree of Doctor of Philosophy in Chemical Engineering, 2018, pp. 1-217(248 Pages).

* cited by examiner

FERMENTATION PROCESS

BACKGROUND

The genus *Bordetella* is the causative agent for a number of bacterial diseases, for example *Bordetella pertussis* (also known as *Haemophilus pertussis*) is responsible for whooping cough, a respiratory disease that can be severe in infants and young children. The clinical course of the disease is characterised by paroxysms of rapid coughs followed by inspiratory effort, often associated with a characteristic 'whooping' sound. In serious cases, oxygen deprivation can lead to brain damage: however, the most common complication is secondary pneumonia.

Whooping cough is usually considered to be caused by *B. pertussis*, but occasionally *B. parapertussis* is isolated from patients with typical signs and symptoms of whooping cough. *B. parapertussis* infection is of lower frequency than *B. pertussis* with 5-10% of whooping cough being associated with *B. parapertussis* (Mertsola (1985) Eur J Clin Microbiol 4: 123; Lautrop (1971) Lancet 1 (7711): 1195-1198). *B. parapertussis* is associated with mild clinical symptoms which, combined with its serological cross-reactivity with *B. pertussis*, makes *B. parapertussis* difficult to diagnose.

The first generation of vaccines against *B. pertussis* were whole cell vaccines, composed of whole killed bacteria. These were introduced in many countries in the 1950s and 1960s and were successful at reducing the incidence of whooping cough. A problem with whole cell *B. pertussis* vaccines is the high level of reactogenicity associated with them. Acellular vaccines containing purified *B. pertussis* proteins are less reactogenic and have been adopted for the vaccination programmes of many countries. Acellular vaccines containing pertussis toxin (PT), filamentous haemagglutinin (FHA) and quite often pertactin (PRN), are widely used and provide effective protection from the severity of whooping cough.

*Bordetella* virulence factors for use in such vaccines are generated by fermenting *Bordetella* and isolating the produced virulence factors, however *Bordetella* species are fastidious organisms which are difficult to grow in high concentrations (Doern, Clin. Infect. Dis. 2000, 30:166-173), furthermore it is difficult to express *Bordetella* virulence factors, in particular pertussis toxin (PT), which is the limiting antigen in multivalent pertussis vaccines.

There remains a need in the art to improve the efficiency of *Bordetella* fermentation and virulence factor production, especially PT production, for large scale manufacturing. The present inventors have surprisingly found that a medium conditioning step carried out prior to inoculation significantly improves several measures of *Bordetella* fermentation performance at large scale, including increased PT yield, increased biomass, and decreased fermentation time.

SUMMARY OF THE INVENTION

In a first aspect of the invention there is provided a process for producing a conditioned growth medium comprising:
- a) providing a growth medium;
- b) holding the growth medium at a temperature between about 28° C. and about 35° C. for about 20 to 35 hours; and
- c) optionally stirring and/or aerating the growth medium to produce an oxygen volumetric mass transfer coefficient (kLa) of about 10 h$^{-1}$ to about 130 h$^{-1}$, thereby providing the conditioned growth medium.

More particularly, the first aspect of the invention provides a process for producing a sterile conditioned growth medium comprising:
- a) providing a sterile growth medium;
- b) holding the sterile growth medium at a temperature between about 28° C. and about 35° C. for about 20 to 35 hours; and
- c) stirring and/or aerating the sterile growth medium to produce an oxygen volumetric mass transfer coefficient (kLa) of about 10 h$^{-1}$ to about 130 h$^{-1}$.

thereby providing the sterile conditioned growth medium.

In a second aspect of the invention there is provided a conditioned growth medium produced by a process comprising:
- a) providing a growth medium;
- b) holding the growth medium at a temperature between about 28° C. and about 35° C. for about 20 to 35 hours; and
- c) optionally stirring and/or aerating the growth medium to produce an oxygen volumetric mass transfer coefficient (kLa) of about 10 h$^{-1}$ to about 130 h$^{-1}$.

More particularly, the second aspect of the invention provides a sterile conditioned growth medium produced by a process comprising:
- a) providing a sterile growth medium;
- b) holding the sterile growth medium at a temperature between about 28° C. and about 35° C. for about 20 to 35 hours; and
- c) stirring and/or aerating the sterile growth medium to produce an oxygen volumetric mass transfer coefficient (kLa) of about 10 h$^{-1}$ to about 130 h$^{-1}$.

In a third aspect of the invention there is provided a process for cultivating a *Bordetella* species comprising:
- a) inoculating a conditioned growth medium of the second aspect with at least one *Bordetella* cell to produce a *Bordetella* culture; and
- b) maintaining the *Bordetella* culture under conditions to allow increase in biomass and/or production of at least one *Bordetella* protein.

In a fourth aspect of the invention there is provided a process for producing a *Bordetella* protein comprising:
- a) inoculating a conditioned growth medium of the second aspect with at least one *Bordetella* cell to produce a *Bordetella* culture;
- b) maintaining the *Bordetella* culture under conditions to allow production of at least one *Bordetella* protein; and
- c) isolating said at least one *Bordetella* protein from the culture.

In a fifth aspect of the invention there is provided an isolated *Bordetella* protein produced by a process comprising:
- a) inoculating a conditioned growth medium of the second aspect with at least one *Bordetella* cell to produce a *Bordetella* culture;
- b) maintaining the *Bordetella* culture under conditions to allow production of at least one *Bordetella* protein; and
- c) isolating said at least one *Bordetella* protein from the culture.

In a sixth aspect of the invention there is provided an immunogenic composition comprising an isolated *Bordetella* protein produced by a process comprising:
- a) inoculating a conditioned growth medium of the second aspect with at least one *Bordetella* cell to produce a *Bordetella* culture;

b) maintaining the *Bordetella* culture under conditions to allow production of at least one *Bordetella* protein; and c) isolating said at least one *Bordetella* protein from the culture.

DETAILED DESCRIPTION

Figure 1:
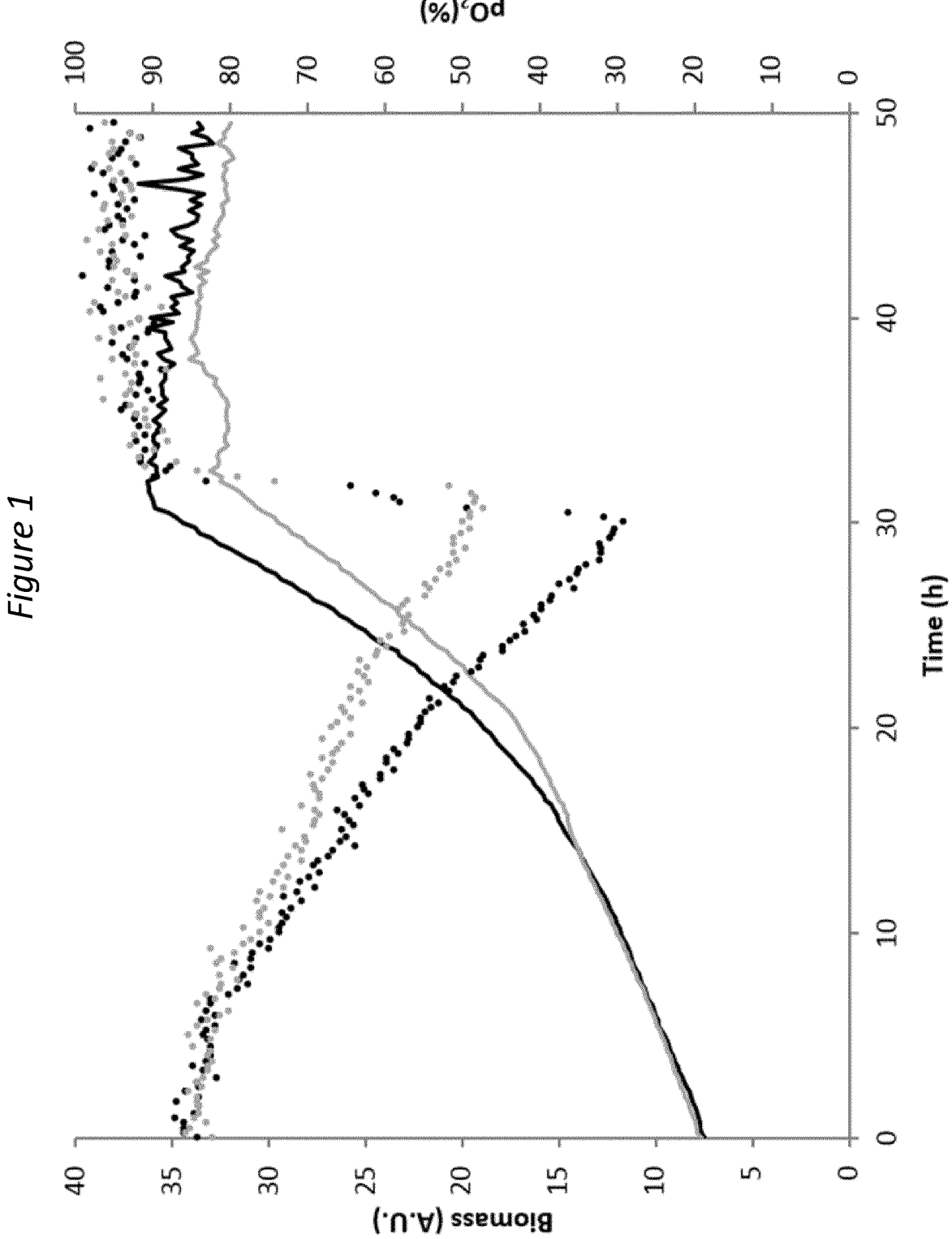
FIG. 1: Changes in biomass (solid lines) and oxygen consumption (dots), during *Bordetella* fermentation in conditioned medium (black) and non-conditioned medium (gray).

The present invention is based on the unexpected observation that adding a medium conditioning step prior to inoculation significantly improves several measures of *Bordetella* fermentation performance, including increased yield of *Bordetella* proteins, increased biomass, and decreased fermentation time. Particularly the step or process is performed using sterile growth medium. More particularly, the step or process is an aseptic process. Yet more particularly, the step or process is an aseptic process performed using sterile growth medium. As used herein, the term "aseptic process" refers to processes and conditions that prevent contamination by exclusion of microorganisms.

As used herein, the term "conditioning" refers to a process by which the sterile growth medium is treated prior to inoculation with bacteria, in other words conditioning is performed in the absence of bacteria and the culture medium is sterile. Conditioning is a process that generally comprises a phase of aeration and/or agitation of the sterile growth medium to improve the performance of subsequent fermentation steps. Particularly, the sterile growth medium remains sterile for the duration of the conditioning process. Thus, preferably, processes for producing a conditioned growth medium of the invention are aseptic processes. Preferably, processes of the invention are aseptic process that produce a sterile conditioned growth medium.

Thus, one aspect of the invention is a process for producing a conditioned growth medium comprising: providing a growth medium: holding the growth medium at a temperature between about 28° C. and about 35° C. for about 20 to 35 hours; and optionally stirring and/or aerating the growth medium to produce an oxygen volumetric mass transfer coefficient (kLa) of about 10 h$^{-1}$ to about 130 h$^{-1}$, thereby providing the conditioned growth medium. More particularly, the invention is a process, particularly an aseptic process, for producing a conditioned growth medium comprising: providing a sterile growth medium; holding the sterile growth medium at a temperature between about 28° C. and about 35° C. for about 20 to 35 hours; and optionally stirring and/or aerating the sterile growth medium to produce an oxygen volumetric mass transfer coefficient (kLa) of about 10 h$^{-1}$ to about 130 h$^{-1}$, thereby providing the conditioned growth medium. The conditioned growth medium, produced by the process from sterile growth medium, is itself sterile, i.e., free from independently replicating living organisms.

A growth medium can be any medium capable of supporting *Bordetella* cell growth. In certain embodiments, the growth medium is the chemically-defined Stainer Scholte (SS) medium, or a modified Stainer Scholte medium (MSS). The composition of Stainer Scholte medium is described in Cohen and Wheeler, American Journal of Public Health (1946) 36:371-376. A medium is a modified Stainer Scholte medium if it contains essentially the same medium components as SS medium at essentially the same concentrations, however, containing modification of the concentration of between 1 and 5 of the medium components, lacking between 1 and 3 of the medium components, or containing between 1 and 20 additional medium components.

In a specific embodiment, the modified Stainer and Scholte medium comprises dimethyl-β-cyclodextrin (e.g., about 1 g/L) and acid casein hydrolysate (e.g., about 10 g/L). In additional embodiments the modified Stainer and Scholte medium comprises L-cysteine (e.g., about 40 mg/L) in place of L-cystine: increased concentration of Na-L-Glutamate (e.g., about 11.84 g/L): reduced concentration of glutathione (e.g., about 150 mg/L); and/or reduced concentration of ascorbic acid (e.g., about 400 mg/L). Thus, in some embodiments, the growth medium is modified Stainer Scholte medium (MSS). In some embodiments, the growth medium is modified Stainer and Scholte medium comprising about 1 g/L of dimethyl-β-cyclodextrin and about 10 g/L of acid casein hydrolysate. In some embodiments, the growth medium is modified Stainer and Scholte medium comprising about 40 mg/L of L-cysteine in place of L-cystine, about 11.84 g/L of Na-L-Glutamate, about 150 mg/L of glutathione, and/or about 400 mg/L of ascorbic acid (e.g., about 400 mg/L).

Compounds that influence production of virulence factors from *Bordetella pertussis* often act by modulating the bvg (bordetella virulence genes) genetic locus and hence can be named bvg modulators (see for example EP2809343B). Thus, in some embodiments, the growth medium may comprise at least one bvg modulator selected from the group consisting of niacin, a magnesium salt, a sulphate salt, a phosphate salt, a carbonate salt, sucrose, proline, sodium ions at a concentration greater than 100 mM, an antifoaming agent, glutathione, and a sulphur containing amino acid. In certain embodiments, the bvg modulator is Niacin. In some embodiments, the growth medium is modified Stainer Scholte medium comprising Niacin.

Conditioning Process Parameters: Temperature. Duration and kLa

In one aspect of the invention, conditioning is accomplished by holding a sterile growth medium at a defined temperature for a defined period of time prior to use in fermentation. In one embodiment, the sterile growth medium is held at a temperature of between about 28° C. and about 35° C. In another embodiment the sterile growth medium is held at a temperature between about 29° C. and about 33° C., or between about 30° C. and about 32° C. In specific embodiments, the sterile growth medium is held at about 29, 30, 31, 32 or 33° C. In additional embodiments, the sterile growth medium is held at about 30.0, 30.2, 30.4, 30.6, 30.8, 31.0, 31.2, 31.4, 31.6, 31.8, or 32.0° C.

In certain embodiments, the sterile growth medium is held at the desired temperature for about 20 to 35 hours. In another embodiment, the sterile growth medium is held at the desired temperature for about 25 to 35 hours or about 30 to 35 hours. In specific embodiments, the sterile growth medium is held at the desired temperature, for example at about 31° C., for about 29, 30, 31, 32, 33, 34 or 35 hours. In a preferred embodiment, the sterile growth medium is held at about 31° C. for about 32 hours.

In certain embodiments, growth medium conditioning is carried out at a scale of at least 10 L, at least 100 L, at least 800, or at least 1000 L of growth medium. In particular embodiments, growth medium conditioning is carried out at a scale of about 10-100 L, about 100-500 L, about 500-1000 L, about 1000-1500 L, about 1500-2000 L, about 1000 L-2500 L or about 1500 L-2500 L.

In some embodiments, the process of the instant invention requires maintaining the sterile growth medium at a constant kLa throughout the conditioning process. kLa, the oxygen volumetric mass transfer coefficient, is a measure of the rate at which oxygen enters the medium. The higher the kLa, the greater the rate at which oxygen is introduced into the medium. Several factors including the medium volume and composition, agitation (e.g. stirring), aeration, pressure, and temperature will influence the kLa of a particular growth medium preparation.

Oxygen can be introduced into the sterile growth medium by agitation (e.g., stirring) and/or aeration (bubbling compressed air through the culture). Where different concentrations of oxygen are present in the air introduced into the medium, the flow rate should be adapted to take account of this. For instance, where a supply of 100% oxygen is introduced into the medium, the flow rate would be correspondingly lower. Where gas containing less oxygen than air is introduced into the medium, a higher flow rate could be applied. Where aeration is achieved by bubbling compressed air through the culture, particularly the compressed air is sterile filtered through a filter, more particularly a filter having pores small enough to prevent microorganisms or spores from entering the vessel (for example, bioreactor, fermenter or medium preparation tank) with the air, preferably a filter with a cutoff in the range of from about 0.2 μm to about 0.45 μm.

kLa can be measured using methods known in the art, for example as described in Example 1 of US2008/0193475. The method involves setting up the bioreactor with the conditions of medium volume, temperature, pressure, agitation and aeration for which the kLa is to be measured, gassing out by replacing the air with nitrogen gas, gassing in by restoring air aeration and measuring the rate at which $pO_2$ returns to its steady state level.

kLa is calculated by plotting the log $(100\text{-}pO_2\%)$ against time. The angular coefficient of the linear part of the graph corresponds to $-kLa$. Typically, only data between 20% and 80% $pO_2$ are considered.

The kLa of a medium conditioning step or process is influenced by a number of factors including the stirring speed and aeration flow rate of the medium. A constant kLa may be maintained while for instance decreasing the stirring speed of the medium and increasing the aeration rate, or vice versa. In an embodiment, both the stirring speed and the aeration rate of the growth medium are constant during medium conditioning. In one embodiment, the growth medium is stirred continuously throughout the duration of conditioning. In another embodiment the growth medium is aerated continuously throughout the duration of conditioning. In another embodiment, both stirring and aerating occur continuously throughout the duration of conditioning.

Growth medium conditioning is carried out, for example, at a kLa of between about 10-200 $h^{-1}$, 10-150 $h^{-1}$, 10-100 $h^{-1}$, 10-80 $h^{-1}$, 10-50 $h^{-1}$, 10-40 $h^{-1}$, 10-30 $h^{-1}$, 20-150 $h^{-1}$, 20-100 $h^{-1}$, 20-50 $h^{-1}$, 20-60 $h^{-1}$, 20-80 $h^{-1}$, 20-30 $h^{-1}$, 20-40 $h^{-1}$, 30-60 $h^{-1}$, 60-80 $h^{-1}$, 60-150 $h^{-1}$ or 60-200 $h^{-1}$. In particular embodiments, growth medium conditioning is carried out at a kLa of about 10 $h^{-1}$ to about 130 $h^{-1}$, about 60 $h^{-1}$ to about 130 $h^{-1}$, or about 90 $h^{-1}$. In a preferred embodiment, the kLa of the growth medium is held at about 90 $h^{-1}$.

For a volume of 10-30 litres, a kLa of 10-30 $h^{-1}$ is achieved for example by using an airflow or aeration rate of 1-5 litres/min and an agitation speed of 200-400 rpm (revolutions per minute), for example an aeration rate of 2-4 litres/min and an agitation speed of 250-350 rpm.

For a volume of 30-250 litres, a kLa of 30-60 $h^{-1}$ is achieved for example by using an airflow rate of 15-25 litres/min and an agitation speed of 150-250 rpm, for example by using an airflow rate of 20-25 litres/min and an agitation speed of 200-250 rpm, for example by using an airflow rate of 15-20 litres/min and an agitation speed of 200-250 rpm.

In a specific embodiment, growth medium conditioning is carried out at about 31 deg C, for about 32 h, at a kLa of about 90 $h^{-1}$.

The invention further provides a conditioned growth medium produced by the process of the invention. The conditioned growth medium is sterile. By "sterile" is intended to mean that the growth medium is free, or essentially free, of bacterial cells, e.g., prior to inoculation with *Bordetella* cells.

Thus, in one aspect the invention provides a conditioned growth medium produced by a process, particularly an aseptic process, comprising:

a) providing a sterile growth medium;

b) holding the sterile growth medium at a temperature between about 28° C. and about 35° C. for about 20 to 35 hours; and c) stirring and/or aerating the sterile growth medium to produce an oxygen volumetric mass transfer coefficient (kLa) of about 10 h$^{-1}$ to about 130 h$^{-1}$.

Particularly, in step c) the sterile growth medium is stirred and/or aerated continuously for the duration of step b). In some embodiments, in step c) the sterile growth medium is stirred continuously for the duration of step b). In other embodiments, in step c) the sterile growth medium is aerated continuously for the duration of step b). In some embodiments, in step c) the sterile growth medium is stirred and aerated continuously for the duration of step b).

Bordetella Fermentation Process

In one aspect, the invention provides a process for cultivating a Bordetella species comprising: inoculating a conditioned growth medium produced as described herein, with at least one Bordetella cell to produce a Bordetella culture; and maintaining the Bordetella culture under conditions to allow increase in biomass and/or production of at least one Bordetella protein. Particularly, the conditioned growth medium is sterile prior to inoculation with the at least one Bordetella cell.

In another aspect of the invention there is provided a process for producing a Bordetella protein comprising:

a) inoculating a conditioned growth medium produced as described herein with at least one Bordetella cell to produce a Bordetella culture;

b) maintaining the Bordetella culture under conditions to allow production of at least one Bordetella protein; and c) isolating said at least one Bordetella protein from the culture.

Preferably, the process for producing a Bordetella protein comprises:

a) inoculating a sterile conditioned growth medium produced as described herein with at least one Bordetella cell to produce a Bordetella culture;

b) maintaining the Bordetella culture under conditions to allow production of at least one Bordetella protein; and c) isolating said at least one Bordetella protein from the culture.

In a further aspect of the invention there is provided an isolated Bordetella protein produced by a process comprising:

a) inoculating a conditioned growth medium produced as described herein with at least one Bordetella cell to produce a Bordetella culture;

b) maintaining the Bordetella culture under conditions to allow production of at least one Bordetella protein; and c) isolating said at least one Bordetella protein from the culture.

Preferably, the isolated Bordetella protein is produced by a process comprising:

a) inoculating a sterile conditioned growth medium produced as described herein with at least one Bordetella cell to produce a Bordetella culture;

b) maintaining the Bordetella culture under conditions to allow production of at least one Bordetella protein; and c) isolating said at least one Bordetella protein from the culture.

In some embodiments, the Bordetella species is Bordetella pertussis or Bordetella parapertussis. In one embodiment, the at least one Bordetella protein is selected from the group consisting of pertussis toxin (PT), filamentous haemagglutinin (FHA), pertactin (PRN: also known as 69K) and adenylate cyclase (AC). In a preferred embodiment, the at least one Bordetella protein is pertussis toxin, for example, a genetically detoxified pertussis toxin (PTg). In some embodiments, the pertussis toxin is a genetically detoxified pertussis toxin in which two catalytic residues of the S1 subunit (Arg9 and Glu129) are mutated to Lys9 and Gly129 (referred to as the PT-9K/129G mutant).

Biomass may be quantified by determining the optical density (OD), for example at 650 nm (also referred to as OD$_{650}$). In one embodiment, the density of the bacteria reaches at least 10, at least 15, at least 20, at least 30, at least 40, at least 50, at least 60, or at least 70 OD units measured at 650 nm at the end of fermentation. Optical density may also be expressed in Absorbance Units (A.U.). The end of fermentation is defined as the time in culture at which dissolved oxygen (pO$_2$) reaches a minimum and begins to climb.

In another embodiment, the invention provides an immunogenic composition comprising an isolated Bordetella protein produced by a process of the invention. Immunogenic compositions of the invention may further comprise one or more pharmaceutically acceptable excipients, adjuvants and/or additional antigens.

Conditioned growth medium prepared according to processes of the invention provides certain advantages in the fermentation of Bordetella cultures. For example, the processes of the invention may result in at least one Bordetella protein being produced at a yield that is at least 5%, 10%, 15%, 20%, 25%, or 30% higher than the yield produced from the same process carried out with non-conditioned growth medium. In a specific embodiment, the yield of PT is increased at least 10%, and the yield of filamentous haemagglutinin is unchanged or higher than the yield produced from the same process carried out with non-conditioned growth medium. Non-conditioned growth medium used for comparison is growth medium that has not undergone treatment or conditioning according to the process of the invention, for example, freshly prepared growth medium. One skilled in the art will appreciate that the conditioned and non-conditioned growth medium used for comparison will be of the same type, i.e. enabling a like-for like comparison.

In another embodiment, the fermentation time, defined as the time from inoculation to the point at which the pO$_2$ level reaches a minimum and begins to climb, is at least 10% shorter than the fermentation time for the same process carried out with non-conditioned growth medium.

In another embodiment, the Bordetella fermentation process of the invention produces a biomass at the end of fermentation that is at least 10% higher than the biomass produced by the same process carried out with non-conditioned growth medium.

In another embodiment, the Bordetella fermentation process of the invention further comprises the step of purifying one or more Bordetella proteins from the Bordetella culture.

In a specific embodiment, the invention provides an aseptic process for producing a conditioned growth medium comprising: providing a sterile modified Stainer and Scholte growth medium: holding the sterile growth medium at a temperature between about 30-32° C. for about 31-33 hours; and stirring and/or aerating the sterile growth medium to produce an oxygen volumetric mass transfer coefficient (kLa) of about 90 h$^{-1}$, thereby providing the conditioned growth medium. More particularly, an aseptic process for producing a conditioned growth medium comprising: providing a sterile modified Stainer and Scholte growth medium: holding the sterile growth medium at a temperature between about 30-32° C. for about 31-33 hours; and stirring and aerating the sterile growth medium to produce an oxygen volumetric mass transfer coefficient (kLa) of about 90 h$^{-1}$, thereby providing the conditioned growth medium.

In a specific embodiment, the invention provides an aseptic process for producing a conditioned growth medium comprising: providing a sterile modified Stainer and Scholte growth medium comprising about 1 g/L dimethyl-β-cyclodextrin, about 10 g/L acid casein hydrolysate, about 40 mg/L L-cysteine in place of L-cystine, about 11.84 g/L Na-L-Glutamate; about 150 mg/L glutathione and about 400 mg/L ascorbic acid; holding the sterile growth medium at a temperature of about 31° C. for about 32 hours; and stirring and/or aerating the sterile growth medium to produce an oxygen volumetric mass transfer coefficient (kLa) of about 90 h$^{-1}$, thereby providing the conditioned growth medium. More particularly, an aseptic process for producing a conditioned growth medium comprising: providing a sterile modified Stainer and Scholte growth medium comprising about 1 g/L dimethyl-β-cyclodextrin, about 10 g/L acid casein hydrolysate, about 40 mg/L L-cysteine in place of L-cystine, about 11.84 g/L Na-L-Glutamate: about 150 mg/L glutathione and about 400 mg/L ascorbic acid: holding the sterile growth medium at a temperature of about 31° C. for about 32 hours; and stirring and aerating the sterile growth medium to produce an oxygen volumetric mass transfer coefficient (kLa) of about 90 h$^{-1}$, thereby providing the conditioned growth medium.

Particular Embodiments

Embodiment 1. A process for producing a conditioned growth medium comprising: (i) providing a growth medium: (ii) holding the growth medium at a temperature between about 28 and about 35° C. for about 20 to 35 hours; and (iii) optionally stirring and/or aerating the growth medium to produce an oxygen volumetric mass transfer coefficient (kLa) of about 10 h$^{-1}$ to about 130 h$^{-1}$, thereby providing the conditioned growth medium.

Embodiment 2. The process of embodiment 1, wherein step b) is carried out at a temperature between about 29° C. and about 33° C., about 30° C. and about 32° C., or about 31° C.

Embodiment 3. The process of embodiments 1-2, wherein step b) is carried out for about 25 to 35 hours, about 30 to 35 hours, or about 32 hours.

Embodiment 4. The process of embodiments 1-3, wherein step c) comprises stirring the growth medium continuously for the duration of step b).

Embodiment 5. The process of embodiment 4, wherein the stirring is at a stirring speed that produces an oxygen volumetric mass transfer coefficient (kLa) of about 60 h$^{-1}$ to about 130 h$^{-1}$, or about 90 h$^{-1}$.

Embodiment 6. The process of embodiments 1-5, wherein step c) comprises aerating the growth medium continuously for the duration of step b).

Embodiment 7. The process of embodiment 6, wherein the aerating is at a flow rate that produces an oxygen volumetric mass transfer coefficient (kLa) of about 60 h$^{-1}$ to about 130 h$^{-1}$, or about 90 h$^{-1}$.

Embodiment 8. The process of embodiments 1-7, wherein step c) comprises stirring and aerating the growth medium continuously for the duration of step b).

Embodiment 9. The process of embodiment 8, wherein the stirring and aerating are at a stirring speed and flow rate that produce an oxygen volumetric mass transfer coefficient (kLa) of about 60 h$^{-1}$ to about 130 h$^{-1}$ or about 90 h$^{-1}$.

Embodiment 10. The process of embodiments 1-9, wherein the process is carried out at a scale of at least 10 L, at least 100 L or at least 1000 L of growth medium.

Embodiment 11. A conditioned growth medium produced by the process of embodiments 1-10.

Embodiment 12. A process for cultivating a *Bordetella* species comprising: (i) inoculating the conditioned growth medium of embodiment 11 with at least one *Bordetella* cell to produce a *Bordetella* culture; and (ii) maintaining the *Bordetella* culture under conditions to allow increase in biomass and/or production of at least one *Bordetella* protein.

Embodiment 13. A process for producing a *Bordetella* protein comprising: (i) inoculating the conditioned growth medium of embodiment 11 with at least one *Bordetella* cell to produce a *Bordetella* culture: (ii) maintaining the *Bordetella* culture under conditions to allow production of at least one *Bordetella* protein; and (iii) isolating said at least one *Bordetella* protein from the culture.

Embodiment 14. The process of embodiments 12-13, wherein the at least one *Bordetella* protein is selected from the group consisting of pertussis toxin, filamentous haemagglutinin, pertactin and adenylate cyclase.

Embodiment 15. The process of embodiments 12-14, wherein the at least one *Bordetella* protein is produced at a yield that is at least 10% higher than the yield produced from the same process carried out with non-conditioned growth medium.

Embodiment 16. The process of embodiments 12-15, wherein the at least one *Bordetella* protein is pertussis toxin, for example a genetically detoxified pertussis toxin.

Embodiment 17. The process of embodiments 12-16, wherein the at least one *Bordetella* protein is a genetically detoxified pertussis toxin in which two catalytic residues of the S1 subunit (Arg9 and Glu129) are mutated to Lys9 and Gly129.

Embodiment 18. The process of embodiment 16, wherein the yield of filamentous haemagglutinin is unchanged or higher than the yield produced from the same process carried out with non-conditioned growth medium.

Embodiment 19. The process of embodiments 12-18, wherein the fermentation time is at least 10% shorter than the fermentation time for the same process carried out with non-conditioned growth medium.

Embodiment 20. The process of embodiments 12-19, wherein the *Bordetella* culture has a biomass at the end of fermentation that is at least 10% higher than the biomass produced by the same process carried out with non-conditioned growth medium.

Embodiment 21. The process of embodiments 12-20, wherein the process further comprises the step of purifying one or more *Bordetella* proteins from the *Bordetella* culture.

Embodiment 22. The process of embodiments 1-10, wherein the growth medium is sterile.

Embodiment 23. An isolated *Bordetella* protein produced by the process of embodiments 12-22.

Embodiment 24. An immunogenic composition comprising the isolated *Bordetella* protein of embodiment 23.

Embodiment 25. An aseptic process for producing a conditioned growth medium comprising: (i) providing a sterile growth medium; (ii) holding the sterile growth medium at a temperature between about 28 and about 35° C. for about 20 to 35 hours; and (iii) stirring and/or aerating the sterile growth medium to produce an oxygen volumetric mass transfer coefficient (kLa) of about 10 h$^{-1}$ to about 130 h$^{-1}$, thereby providing the conditioned growth medium.

Embodiment 26. The aseptic process of embodiment 25, wherein step b) is carried out at a temperature between about 29° C. and about 33° C., about 30° C. and about 32° C., or about 31° C.

Embodiment 27. The aseptic process of embodiment 25 or 26, wherein step b) is carried out for about 25 to 35 hours, about 30 to 35 hours, or about 32 hours.

Embodiment 28. The aseptic process of embodiments 25, 26 or 27, wherein step c) comprises stirring the sterile growth medium continuously for the duration of step b).

Embodiment 29. The aseptic process of embodiment 28, wherein the stirring is at a stirring speed that produces an oxygen volumetric mass transfer coefficient (kLa) of about 60 h$^{-1}$ to about 130 h$^{-1}$, or about 90 h$^{-1}$.

Embodiment 30. The aseptic process of embodiments 25 to 29, wherein step c) comprises aerating the sterile growth medium continuously for the duration of step b).

Embodiment 31. The aseptic process of embodiment 30, wherein the aerating is at a flow rate that produces an oxygen volumetric mass transfer coefficient (kLa) of about 60 h$^{-1}$ to about 130 h$^{-1}$, or about 90 h$^{-1}$.

Embodiment 32. The aseptic process of embodiments 25 to 31, wherein step c) comprises stirring and aerating the sterile growth medium continuously for the duration of step b).

Embodiment 33. The aseptic process of embodiment 32, wherein the stirring and aerating are at a stirring speed and flow rate that produce an oxygen volumetric mass transfer coefficient (kLa) of about 60 h$^{-1}$ to about 130 h$^{-1}$ or about 90 h$^{-1}$.

Embodiment 34. The aseptic process of embodiments 25 to 33, wherein the process is carried out at a scale of at least 10 L, at least 100 L or at least 1000 L of sterile growth medium.

Embodiment 35. A conditioned growth medium produced by the aseptic process of embodiments 25 to 34.

Embodiment 36. A process for cultivating a *Bordetella* species comprising: (i) inoculating the conditioned growth medium of embodiment 35 with at least one *Bordetella* cell to produce a *Bordetella* culture; and (ii) maintaining the *Bordetella* culture under conditions to allow increase in biomass and/or production of at least one *Bordetella* protein.

Embodiment 37. A process for producing a *Bordetella* protein comprising: (i) inoculating the conditioned growth medium of embodiment 35 with at least one *Bordetella* cell to produce a *Bordetella* culture: (ii) maintaining the *Bordetella* culture under conditions to allow production of at least one *Bordetella* protein; and (iii) isolating said at least one *Bordetella* protein from the culture.

Embodiment 38. The process of embodiment 36 or 37, wherein the at least one *Bordetella* protein is selected from the group consisting of pertussis toxin, filamentous haemagglutinin, pertactin and adenylate cyclase.

Embodiment 39. The process of embodiments 36, 37 or 38, wherein the at least one *Bordetella* protein is produced at a yield that is at least 10% higher than the yield produced from the same process carried out with non-conditioned growth medium.

Embodiment 40. The process of embodiments 36 to 39, wherein the at least one *Bordetella* protein is pertussis toxin, for example a genetically detoxified pertussis toxin.

Embodiment 41. The process of embodiments 36 to 40, wherein the at least one *Bordetella* protein is a genetically detoxified pertussis toxin in which two catalytic residues of the S1 subunit (Arg9 and Glu129) are mutated to Lys9 and Gly129.

Embodiment 42. The process of embodiments 40 or 41, wherein the yield of filamentous haemagglutinin is unchanged or higher than the yield produced from the same process carried out with non-conditioned growth medium.

Embodiment 43. The process of embodiments 36 to 42, wherein the fermentation time is at least 10% shorter than the fermentation time for the same process carried out with non-conditioned growth medium.

Embodiment 44. The process of embodiments 36 to 43, wherein the *Bordetella* culture has a biomass at the end of fermentation that is at least 10% higher than the biomass produced by the same process carried out with non-conditioned growth medium.

Embodiment 45. The process of embodiments 36 to 44, wherein the process further comprises the step of purifying one or more *Bordetella* proteins from the *Bordetella* culture.

Embodiment 46. The process of any preceding embodiment wherein, the growth medium is modified Stainer Scholte medium (MSS), optionally comprising Niacin.

Embodiment 47. The process of embodiment 46, wherein the growth medium is modified Stainer and Scholte medium comprising about 1 g/L of dimethyl-β-cyclodextrin and about 10 g/L of acid casein hydrolysate.

Embodiment 48. The process of embodiment 46 or 47, wherein the growth medium is modified Stainer and Scholte medium comprising about 40 mg/L of L-cysteine in place of L-cystine: about 11.84 g/L of Na-L-Glutamate: about 150 mg/L of glutathione; and/or about 400 mg/L of ascorbic acid (e.g., about 400 mg/L).

Embodiment 49. An aseptic process for producing a sterile conditioned growth medium comprising: (a) providing a sterile growth medium: (b) holding the sterile growth medium at a temperature between about 29° C. and about 33° C., about 30° C. and about 32° C., or about 31° C. for about 25 to 35 hours, about 30 to 35 hours, or about 32 hours; and (c) stirring and/or aerating the sterile growth medium continuously for the duration of step (b) to produce an oxygen volumetric mass transfer coefficient (kLa) of about 60 h$^{-1}$ to about 130 h$^{-1}$, or about 90 h$^{-1}$, thereby providing the sterile conditioned growth medium; wherein, the growth medium is modified Stainer Scholte medium (MSS), optionally comprising Niacin.

General

Unless otherwise noted, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise.

Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%. Unless the context requires otherwise, the word "between" when used in expressing a range of values (e.g., "between X and Y" or "between about X and about Y") is intended to be inclusive of the end-points of the range (i.e., including X and Y).

The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The term "consisting of" means "including and limited to." The term "consisting essentially of" means that the composition or method may include additional ingredients and/or steps, but only if the additional ingredients and/or steps do not materially alter the basic and novel characteristics of the claimed composition or method. The abbreviation, "e.g." is derived from the Latin exempli gratia and is used herein to indicate a non-limiting example. Thus, the abbreviation "e.g." is synonymous with the term "for example."

The invention will be further described by reference to the following, non-limiting, examples and figures.

EXAMPLES

Example 1: Demonstration of Medium Conditioning Effect at Laboratory Scale

Preliminary observations indicated that yield variability in a commercial scale *Bordetella* fermentation process may be due to differences in conditioning of the growth medium prior to inoculation. To explore the sources of this variability, the effect of growth medium conditioning prior to inoculation was examined in a laboratory scale model process.

Laboratory-Scale Model

A laboratory scale model was developed to reproduce the three steps of the commercial process: 1) a pre-culturetrain: 2) medium conditioning; and 3) fermentation. The pre-culture train step refers to the steps of pre-culture used to accumulate sufficient biomass for inoculation of the fermentation step. Since the medium conditioning is an aseptic process step taking place in the absence of bacteria, medium conditioning is carried out independently of the pre-culture train step, for example, before, after or in parallel. In the pre-culture, a first shake-flask pre-culture containing 30 ml fresh medium (MSS: derived from the medium of Stainer and Scholte. J. Gen. Microbial. 63:211-220 (1971) by the addition of dimethyl-β-cyclodextrin 1 g/L and acid casein hydrolysate 10 g/L, the replacement of L-cystine 40 mg/L with L-cysteine 40 mg/L, and the use of higher concentrations of Na-L-Glutamate (11.84 g/L), reduced glutathione (150 mg/L) and ascorbic acid (400 mg/L)) was inoculated with 109 *B. pertussis* CFUs and incubated at 35° C., stirring at 150 rpm, for 24 h. The first pre-culture was used to inoculate a second shake-flask pre-culture containing 1000 ml fresh medium (MSS). The second pre-culture was incubated at 35° C., stirring at 150 rpm, for 24 h. Aliquots of the pre-culture train were then used to inoculate conditioned growth medium for fermentation, as described below.

Medium conditioning was carried out in parallel to the pre-culture train. 1 L of sterile growth medium (same type as used for pre-culture) was aseptically transferred in a 1 L bioreactor (BioBlock platform (4×1 L bioreactor), Eppendorf) and held for 40 hours at 35° C., airflow rate of 20 L sparged air per hour, stirring speed of 430 rpm (kLa of 60 h$^{-1}$). As a control, non-conditioned growth medium was held at 4° C. without further processing. The preparation of conditioned and non-conditioned media was carried out four times (Prep 1, Prep 2, Prep 3, Prep 4) using the same procedures.

The fermentation step was carried out at small scale by inoculating conditioned and non-conditioned medium with the pre-culture train *Bordetella* inoculum, and incubating the cultures under standard conditions (35° C., kLa of at least 90 h$^{-1}$) in small-scale fermentation vessels (<1 L).

Measures of Fermentation Performance

Assessment of fermentation performance, as indicated by biomass, PT yield and fermentation time, was repeated at least 3 times per preparation. In-line measurements of biomass, dissolved oxygen pressure (pO$_2$) and pH were recorded throughout the fermentation. The start of fermentation was defined as the time at which the *Bordetella* pre-culture train was added to the fermentation vessel. The end of fermentation was defined as the timepoint at which dissolved oxygen (pO$_2$) reaches a minimum and begins to climb back toward 100%. The inflection point in pO$_2$ indicates exhaustion of the carbon source in the culture and transition of cells from growth phase to stationary phase. Fermentation time is therefore the amount of time between the start of fermentation and the end of fermentation.

At the end of fermentation, supernatants were recovered by centrifugation (14000 g, 10 min RT), filtered (0.22 μm filter mesh) and stored at −20° C. for further analysis. Pertussis toxin (PT) levels at end of fermentation were assayed by ELISA using standard methods.

Results

The results are summarized in Table 1 as average percentage change relative to non-conditioned medium [Conditioned/Non-Conditioned-1 (%)]. For all four replicates (Preps 1-4), pertussis toxin levels at end of fermentation were increased at least 10% in conditioned medium as compared to unconditioned medium. For three of the preparations (Preps 2-3), there was a corresponding increase in end-of-fermentation biomass in conditioned versus non-conditioned medium. Finally, a trend towards decreased fermentation time was observed when cultures were grown in conditioned medium as compared to non-conditioned medium.

TABLE 1

|  | Biomass | PT (ELISA) | Fermentation Time |
|---|---|---|---|
| Prep 1 | −7.0% | +13.2% | −7.2% |
| Prep 2 | +52.3% | +15.2% | −4.9% |
| Prep 3 | +27.8% | +22.6% | −12.3% |
| Prep 4 | +44.9% | +33.0% | −5.7% |

The growth kinetics of Prep 2 are presented in FIG. 1 as a representative example of the four preparations. *Bordetella* cell growth (biomass) in conditioned medium (solid black line) and non-conditioned medium (solid gray line) was similar for the first 15-20 hours of culture. After that, the rate of cell growth was greater in conditioned medium than in non-conditioned medium. Dissolved oxygen dropped as biomass increased, with a more rapid decrease observed in the conditioned medium fermentation. At the end of fermentation, indicated by the rapid re-increase of dissolved oxygen, biomass was significantly higher in the conditioned medium fermentation condition compared to the non-conditioned fermentation condition.

The results of the initial small-scale study indicate that prior medium conditioning has a positive effect on *Bordetella* cell growth and PT production. In particular, significant increases in end-of-fermentation biomass and PT content were observed for fermentations carried out in conditioned medium. A trend towards shorter fermentation times in conditioned medium was also observed. The results of the laboratory scale model confirm observations made at the commercial scale, indicating that the conditioning effect is independent of the scale of fermentation. No significant effect of medium conditioning was observed on pH of medium during cell growth (data not shown).

Without being bound by underlying theory, the observed medium conditioning effect may be related to biochemical modifications, such as oxidation of one or more medium components, occurring during the medium conditioning process which improve cell growth and productivity of virulence factors during the fermentation step.

Example 2: Identification of Process Parameters that Affect Medium Conditioning To better define the conditioning parameters leading to improved *Bordetella* fermentation performance, a design-of-experiment (DoE) study was carried out.

Methods

The impact of three conditioning process parameters on subsequent fermentation performance was evaluated in a central composite design with 3 levels (min/central/max) per parameter as shown in Table 2. The process parameters were temperature of conditioning, duration of conditioning, and the oxygen volumetric mass transfer coefficient (kLa), which is a factor of aeration flowrate and stirring speed.

TABLE 2

Medium Conditioning Process Parameters

| Parameter | Min | Central | Max |
|---|---|---|---|
| Temperature (° C.) | 28 | 35 | 40 |
| kLa ($h^{-1}$) | 10 | 50 | 90 |
| Duration (hours) | 3 | 23 | 43 |

The DoE was carried out in 60 runs performed over 6 weeks (see Table 3). Each week, 3×1 L conditioning bioreactors were filled with 1 L of sterile growth medium freshly prepared as described in Example 1 and conditioned at 3 different pairs of kLa-temperature. During conditioning, each conditioning bioreactor was sampled at three different time-points (3 h, 23 h and 43 h) to examine the effect of conditioning duration. Samples of medium taken at 3 and 23 h were immediately stored at 4° C. to stabilize the sample. After the last sample was taken, the 9 samples of medium from the 3 bioreactors were transferred to small-scale fermentation vessels (<1 L) and inoculated with *Bordetella* pre-culture train prepared as described in Example 1, for evaluation of growth and antigen production.

Fermentation performance indicators were assessed by measuring PT and FHA content (ELISA), biomass content (growth curve and final optical density) and fermentation time (measured as described in Example 1).

Results

Figure 2:
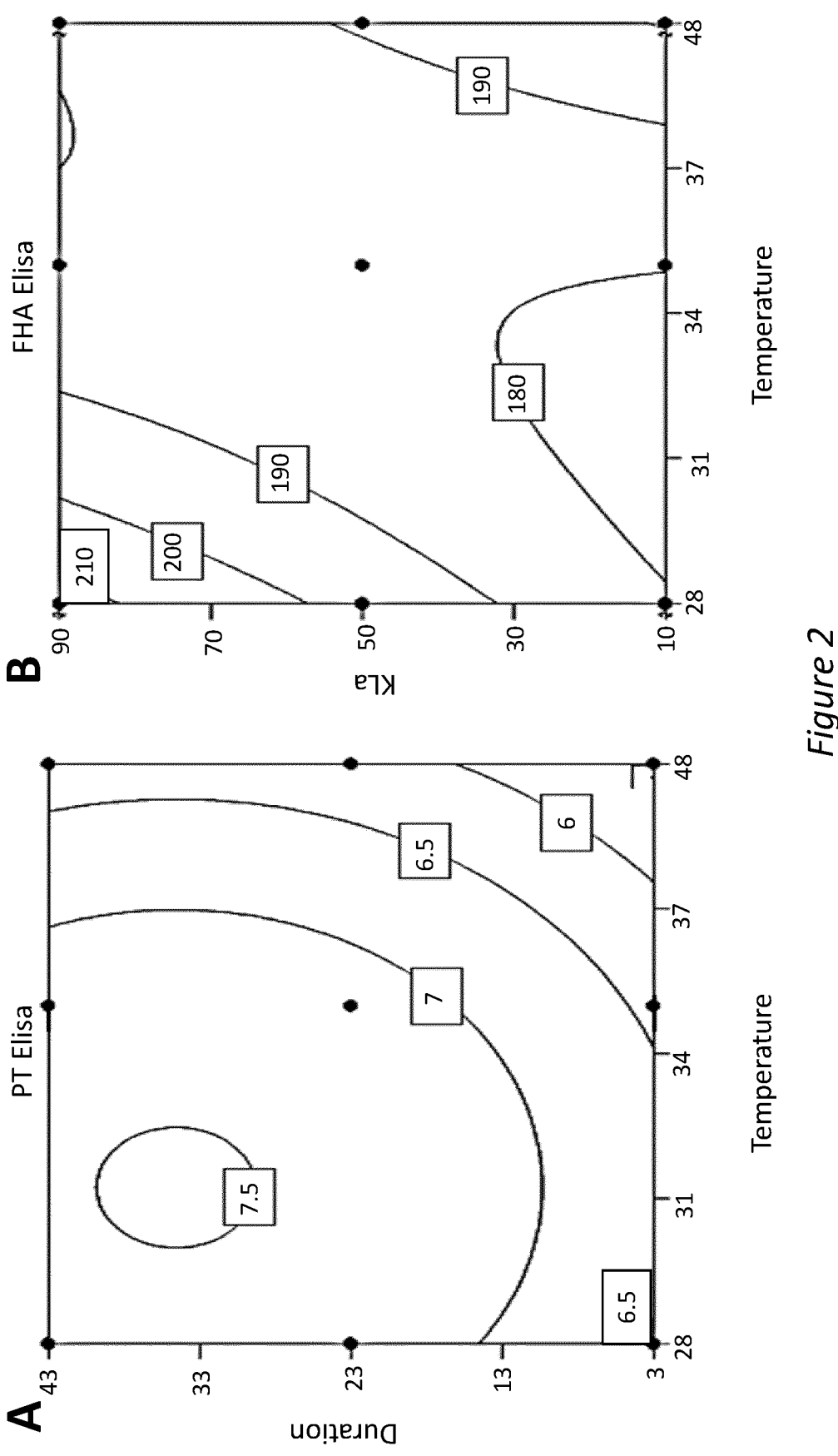
FIG. 2: Surface plots for design-of-experiment evaluating the effect of conditioning process parameters on four measures of *Bordetella* fermentation performance: (A) PT content: (B) FHA content: (C) Biomass; and (D) Fermentation time. The results predict that optimal conditioning parameters for PT yield and biomass production are 34.6 h of conditioning at a temperature of 31.2° C. and kLa around 90 h$^{-1}$.
Figure 2:
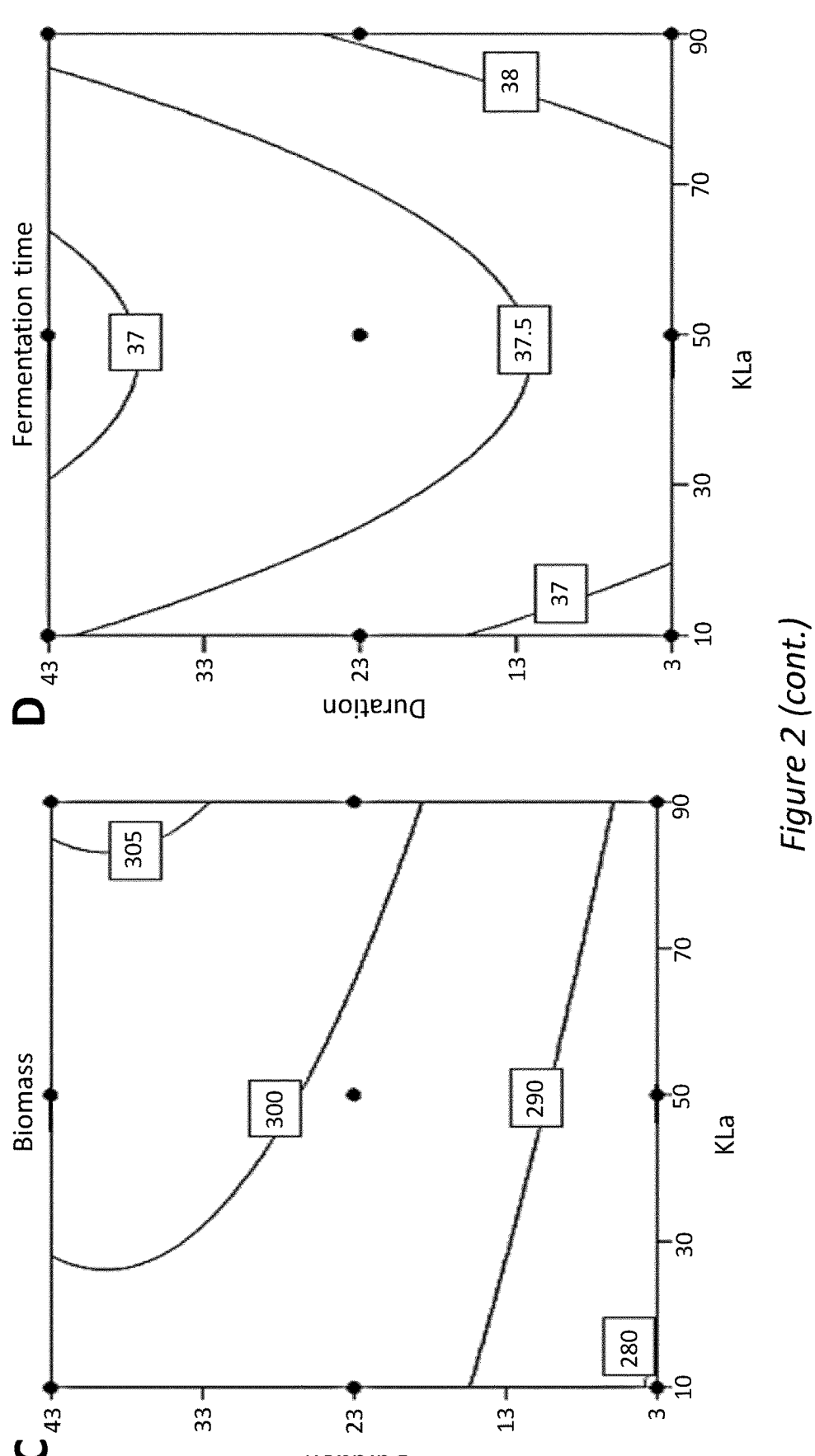

The results are shown in Table 3 and FIG. 2. Fermentation performance indicators were differently influenced by changes in conditioning process parameters. The longer the duration of medium conditioning, the better the resulting biomass and PT content. FHA content was unaffected by increased conditioning duration. Conditioning temperature affected PT production but not growth performance (biomass). Finally, variations in kLa impacted biomass but not PT production.

The results of the DoE predict a design space for conditioning parameter values associated with increased PT (at least 10%) as compared to non-conditioned medium (FIG. 2A-D). The model also predicts that optimal conditioning parameters for PT yield and biomass production are 34.6 h of conditioning at a temperature of 31.2° C. and kLa around 90 $h^{-1}$.

TABLE 3

| | | Conditioning Parameters | | | Fermentation Performance Measures | | | |
|---|---|---|---|---|---|---|---|---|
| Run | Week | Temperature (° C.) | kLa ($h^{-1}$) | Duration (h) | Fermentation time (h) | Biomass (A.U.) | PT (µg/mL) | FHA (µg/mL) |
| 1 | 1 | 28 | 10 | 3 | 38.31 | 249 | 5.59 | 174.11 |
| 2 | 1 | 28 | 10 | 23 | 38.93 | 271 | 6.14 | 176.32 |
| 3 | 1 | 28 | 10 | 43 | 37.25 | 273.6 | 5.95 | 149.25 |
| 4 | 1 | 35 | 50 | 3 | 37.57 | 274.4 | 5.70 | 169.94 |
| 5 | 1 | 35 | 50 | 23 | 36.35 | 268.4 | 5.65 | 132.98 |
| 6 | 1 | 35 | 50 | 43 | 36.23 | 284.6 | 5.24 | 129.07 |
| 7 | 1 | 28 | 90 | 3 | 38.26 | 256.6 | 3.69 | 161.10 |
| 8 | 1 | 28 | 90 | 23 | 38.09 | 276.4 | 6.62 | 200.57 |
| 9 | 1 | 28 | 90 | 43 | 39.12 | 288.9 | 7.00 | 153.92 |
| 10 | 1 | NC | NC | NC | 36.92 | 270.1 | 5.12 | 197.32 |
| 11 | 2 | 40 | 10 | 3 | 39.26 | 288.7 | 6.46 | 206.68 |
| 12 | 2 | 40 | 10 | 23 | 38.95 | 319.1 | 8.69 | 219.92 |
| 13 | 2 | 40 | 10 | 43 | 40.51 | 306.4 | 7.46 | 226.15 |
| 14 | 2 | 35 | 50 | 3 | 40.24 | 291 | 7.92 | 162.08 |
| 15 | 2 | 35 | 50 | 23 | 40.40 | 324.9 | 9.52 | 196.83 |
| 16 | 2 | 35 | 50 | 43 | 41.74 | 334.1 | 9.72 | 228.20 |
| 17 | 2 | 40 | 90 | 3 | 40.63 | 294.6 | 7.44 | 202.25 |
| 18 | 2 | 40 | 90 | 23 | 41.21 | 308.2 | 8.32 | 204.75 |
| 19 | 2 | 40 | 90 | 43 | 40.74 | 331.5 | 9.56 | 221.69 |
| 20 | 2 | NC | NC | NC | 40.24 | 289.4 | 6.89 | 205.41 |
| 21 | 3 | 35 | 10 | 3 | 37.61 | 277.8 | 7.20 | 159.27 |
| 22 | 3 | 35 | 10 | 23 | 37.79 | 296.1 | 7.77 | 190.82 |
| 23 | 3 | 35 | 10 | 43 | 36.60 | 301.5 | 8.91 | 150.98 |
| 24 | 3 | 28 | 50 | 3 | 38.65 | 283.2 | 7.47 | 202.18 |
| 25 | 3 | 28 | 50 | 23 | 36.86 | 295.2 | 8.49 | 194.52 |
| 26 | 3 | 28 | 50 | 43 | 36.06 | 296.6 | 7.51 | 203.41 |
| 27 | 3 | 35 | 50 | 3 | 39.00 | 295.8 | 8.07 | 176.65 |
| 28 | 3 | 35 | 50 | 23 | 36.27 | 295 | 8.55 | 207.20 |
| 29 | 3 | 35 | 50 | 43 | 36.71 | 309.1 | 8.42 | 181.30 |
| 30 | 3 | NC | NC | NC | 37.77 | 282.1 | 6.31 | 234.33 |
| 31 | 4 | 35 | 50 | 3 | 38.00 | 286.4 | 6.14 | 196.78 |
| 32 | 4 | 35 | 50 | 23 | 36.89 | 307 | 7.04 | 195.48 |
| 33 | 4 | 35 | 50 | 43 | 36.56 | 302.3 | 7.06 | 207.69 |

TABLE 3-continued

Design of Experiment results

| | | Conditioning Parameters | | | Fermentation Performance Measures | | | |
|---|---|---|---|---|---|---|---|---|
| Run | Week | Temperature (° C.) | kLa (h$^{-1}$) | Duration (h) | Fermentation time (h) | Biomass (A.U.) | PT (µg/mL) | FHA (µg/mL) |
| 34 | 4 | 40 | 50 | 3 | 37.59 | 282 | 5.60 | 204.34 |
| 35 | 4 | 40 | 50 | 23 | 36.89 | 293.6 | 5.51 | 260.48 |
| 36 | 4 | 40 | 50 | 43 | 36.38 | 302.8 | 5.43 | 216.23 |
| 37 | 4 | 35 | 90 | 3 | 37.73 | 291.8 | 6.20 | 204.82 |
| 38 | 4 | 35 | 90 | 23 | 38.09 | 313.2 | 6.98 | 230.79 |
| 39 | 4 | 35 | 90 | 43 | 37.85 | 309.5 | 7.88 | 177.61 |
| 40 | 4 | NC | NC | NC | 39.89 | 275.1 | 5.48 | NT |
| 41 | 5 | 28 | 10 | 3 | 35.32 | 280.4 | 5.48 | 161.56 |
| 42 | 5 | 28 | 10 | 23 | 35.06 | 292.3 | 6.43 | 169.85 |
| 43 | 5 | 28 | 10 | 43 | 34.86 | 291.7 | 6.61 | 168.32 |
| 44 | 5 | 35 | 50 | 3 | 35.16 | 281.3 | 5.73 | 193.18 |
| 45 | 5 | 35 | 50 | 23 | 34.33 | 290.9 | 6.36 | 151.63 |
| 46 | 5 | 35 | 50 | 43 | 34.52 | 288.4 | 4.88 | 227.00 |
| 47 | 5 | 28 | 90 | 3 | 36.03 | 278.8 | 5.90 | 198.90 |
| 48 | 5 | 28 | 90 | 23 | 34.67 | 297.4 | 5.29 | 204.31 |
| 49 | 5 | 28 | 90 | 43 | 34.68 | 291.4 | 6.82 | 232.72 |
| 50 | 5 | NC | NC | NC | 36.06 | 281.4 | 4.26 | 155.67 |
| 51 | 6 | 40 | 10 | 3 | 37.54 | 284.2 | 4.93 | 177.32 |
| 52 | 6 | 40 | 10 | 23 | 36.86 | 293.4 | 5.91 | 207.68 |
| 53 | 6 | 40 | 10 | 43 | 39.01 | 292.1 | 4.95 | 202.01 |
| 54 | 6 | 35 | 50 | 3 | 37.74 | 277.4 | 5.94 | 197.46 |
| 55 | 6 | 35 | 50 | 23 | 36.92 | 293.9 | 5.93 | 171.34 |
| 56 | 6 | 35 | 50 | 43 | 36.60 | 295.3 | 6.48 | 188.03 |
| 57 | 6 | 40 | 90 | 3 | 38.17 | 282 | 5.28 | 145.18 |
| 58 | 6 | 40 | 90 | 23 | 38.27 | 295.5 | 5.37 | 152.10 |
| 59 | 6 | 40 | 90 | 43 | 37.78 | 298.8 | 5.69 | 182.37 |
| 60 | 6 | NC | NC | NC | 37.84 | 285.2 | 5.57 | 189.28 |

NC: Not conditioned
NT: Not tested

Example 3: Validation of Conditioning Parameters at 1 Liter Bioreactor Scale

To validate the medium conditioning design space for 10% increased PT yield identified in Example 2, the medium conditioning and fermentation processes were carried out at 1 L Bioreactor scale, using conditioning parameters within the predicted design space.

Methods

A platform of 4×1 L-bioreactors (BioBlock, Eppendorf) was used for medium conditioning prior to inoculation. The platform allows conditioning of 4 preparations of media in parallel and to consecutively evaluate their fermentation performances. For the conditioning step, 1 L of sterile growth medium (see Examples 1 and 2) was aseptically transferred into each bioreactor and subjected to the process parameters described in the experimental design (below). If the experimental design required a non-conditioned medium, then one of the four bioreactors was left empty during the conditioning step to allow transfer of non-conditioned medium later (see below).

When the pre-defined duration of medium conditioning was reached, conditioning was stopped. For certain runs, one liter (1 L) of non-conditioned medium (prepared as in Examples 1 and 2) was aseptically transferred to one of the four bioreactors. The following conditions were used in order to calibrate the 100%-dissolved oxygen (DO) level in each bioreactor: temperature (35° C.), atmospheric pressure, air flow rate (2 L sparged air per minute) and stirring speed (300 rpm or rotations per minute). 300 µL of an antifoaming agent (Simethicone 15%) were aseptically added in each bioreactor.

Inoculation was achieved by the addition of 150 mL of *Bordetella pertussis* inoculum (prepared in parallel to conditioning step as described in Examples 1 and 2). During the fermentation, the temperature (35° C.) was maintained at a constant level. Foaming control during the fermentation was performed by addition of antifoam (Simethicone 1.5%). The level of dissolved oxygen was set at 35% to compensate for head pressure applied at larger scale fermentation and regulated by increasing stirring when the DO fell below 35%. The minimum stirring speed was set at 300 rpm: the maximum stirring speed was set at 1100 rpm. The pH was regulated at 7.2 by addition of acetic acid 50% (w/v or weight/volume). At the end of fermentation (defined as in Example 1), biomass yield was determined by measurement of optical density and total quantity of acetic acid added by pH regulation (the latter as an orthogonal method to evaluate biomass content). Pertussis toxin (PT) production in the culture supernatant was determined by ELISA using standard methods.

Experimental Design

In Example 2, a design space resulting in at least 10% increased PT yield was calculated. In this experiment we compared fermentation performance (fermentation time, biomass, PT and FHA yield) of medium conditioned under 3 different sets of process parameters (Processes 2-4 in Table 4) within the calculated PT design space, versus non-conditioned medium (Process 1 in Table 4). Processes 2 and 3 tested the optimum operating parameters for PT yield (32 h at 31° C.) at kLa values of 90 h$^{-1}$ or 60 h$^{-1}$, respectively. Process 4 tested operating parameters at a conditioning temperature of 35° C. and kLa of 60 h$^{-1}$. The experiment was performed once.

TABLE 4

| Process | Duration (hours) | Temperature (° C.) | kLa (h$^{-1}$) |
|---|---|---|---|
| 1 | 32 | 4 | 0 |
| 2 | 32 | 31 | 90 |
| 3 | 32 | 31 | 60 |
| 4 | 32 | 35 | 60 |

Results

Figure 3:
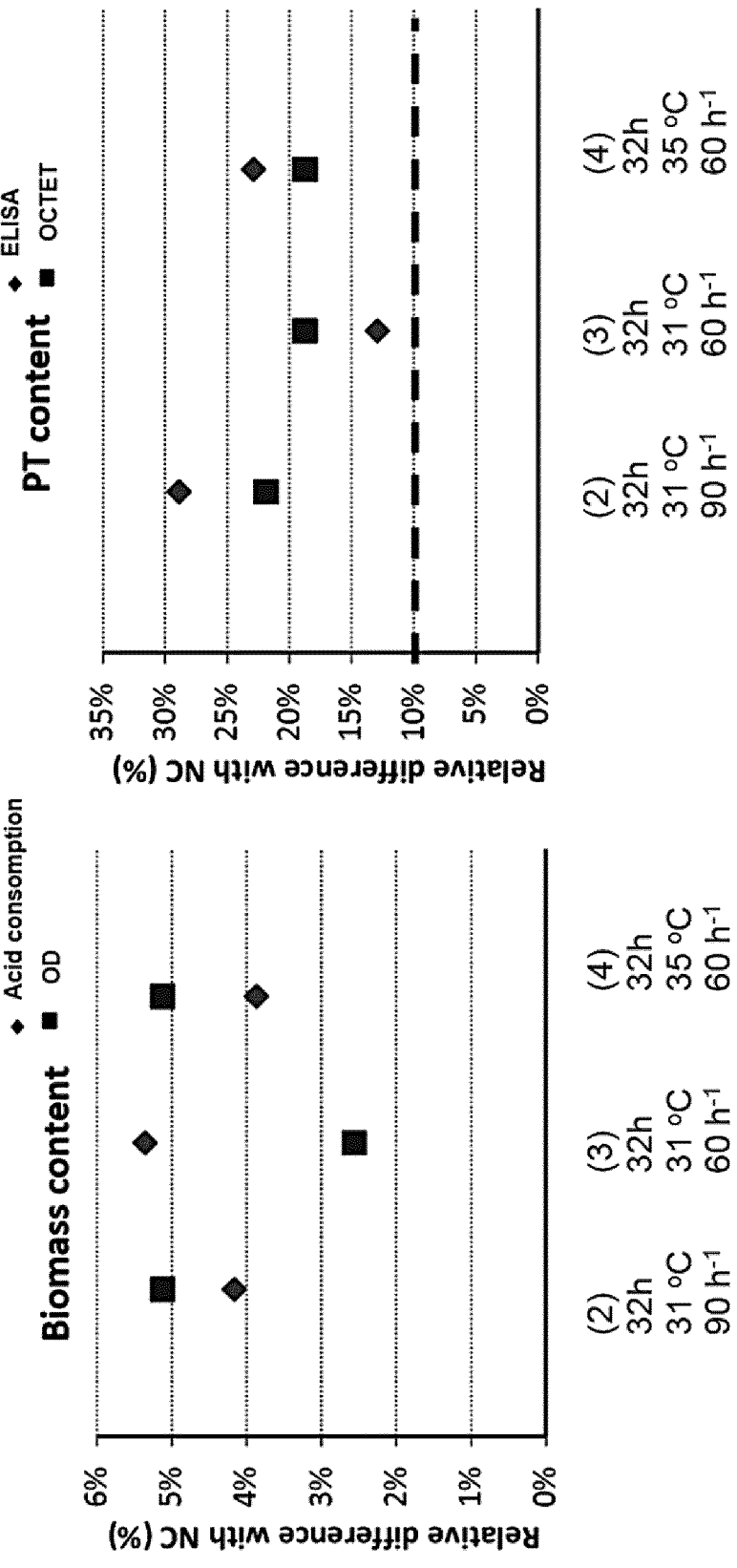
FIG. 3: Validation of conditioning parameters at 1 L bioreactor scale. Right panel: *Bordetella* fermentations carried out in conditioned medium (Processes 2, 3 and 4; see Example 3 for details) yielded PT content that was more than 10% higher than fermentations carried out in non-conditioned medium. Left panel: Biomass content was not significantly affected by temperature or kLa at the 1 L bioreactor scale.

As illustrated in FIG. 3, fermentations carried out in conditioned medium (Processes 2, 3 and 4) yielded PT content that was more than 10% higher than fermentations carried out in non-conditioned medium (right panel). Biomass content was not significantly affected by temperature or kLa at the 1 L bioreactor scale (left panel). These results validate the design space for 10% increased PT yield, identified in the design-of-experiment study (Example 2).

Example 4: Effect of Conditioning Duration at 1 Liter Bioreactor Scale

To explore the effect of conditioning duration across a broader range of time, Example 3 was repeated with a conditioning temperature of 31° C., a kLa value of 90 h$^{-1}$, and conditioning durations of <3 h, 32 h or 56 h (Table 5). The experiment was performed in duplicate.

TABLE 5

| Process | Duration (hours) | Temperature (° C.) | kLa (h$^{-1}$) |
|---|---|---|---|
| 5 | 32 | 4 | 0 |
| 6 | <3 | 31 | 90 |
| 7 | 32 | 31 | 90 |
| 8 | 56 | 31 | 90 |

Results

Figure 4:
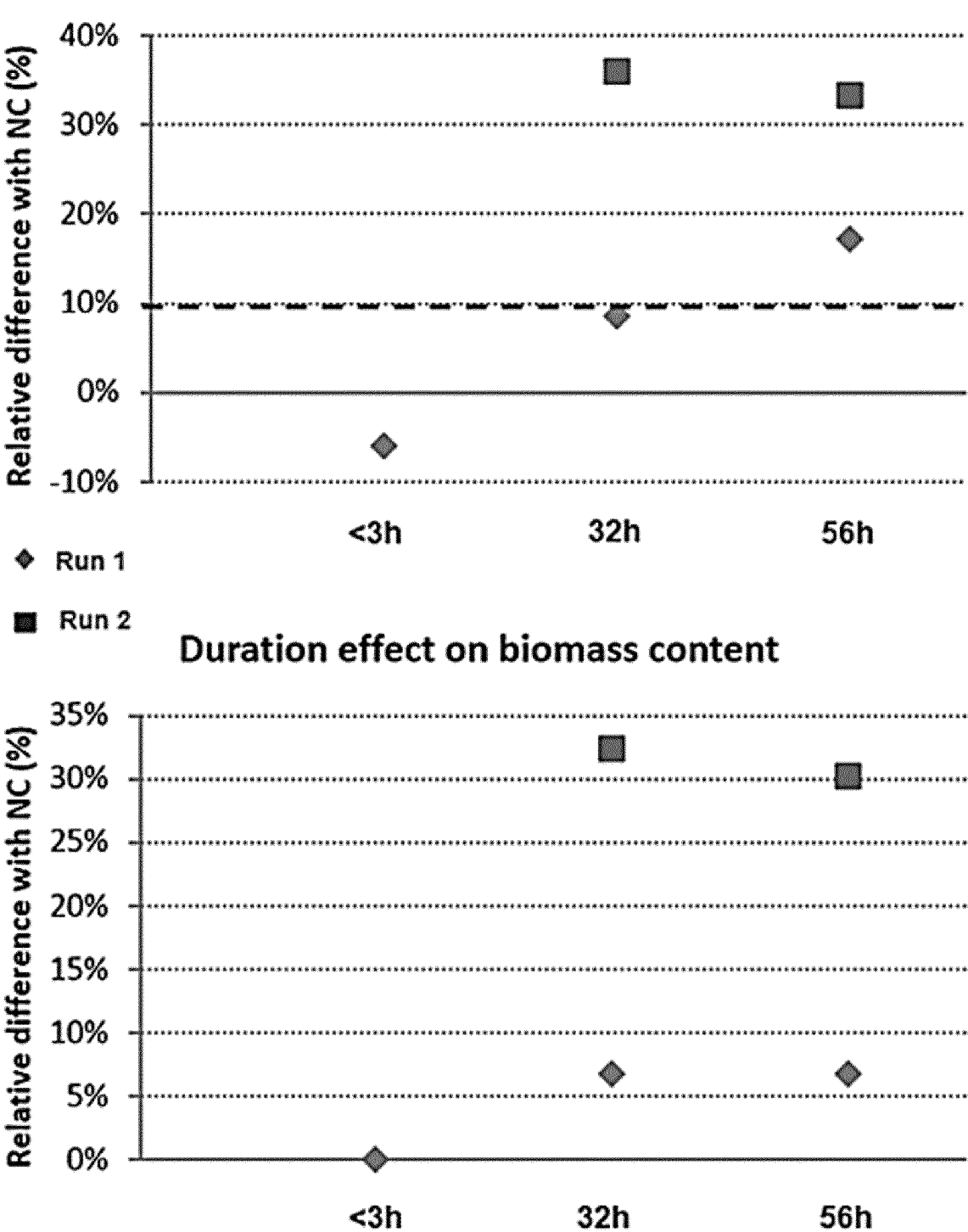
FIG. 4: Effect of conditioning duration on PT content and biomass at 1 L bioreactor scale. Top panel: Medium conditioning for 32 h and 56 h resulted in ≥10% increase in PT content during fermentation compared to non-conditioned medium. Bottom panel: Biomass was increased at 32 h and 56 h.

As shown in FIG. 4, medium conditioning for 32 h and 56 h resulted in ≥10% increase in PT content compared to non-conditioned medium (top panel). Biomass was also increased at 32 h and 56 h (bottom panel). The effect of increasing conditioning duration on PT content and biomass reached a plateau around 32 h.

Example 5: Validation of Optimum Conditioning Parameters at 20 L Bioreactor Scale Optimum medium conditioning parameters were also validated in *Bordetella* fermentations carried out at 20 L bioreactor scale.

Methods

A 20 L fermenter (Biolafitte™) was used for medium conditioning prior to inoculation. 10 L of sterile growth medium, prepared as in Example 1, were aseptically transferred into the 20 L bioreactor, and subjected to the conditioning process parameters summarized in Table 6.

TABLE 6

| Week | Run | Aeration Flowrate (L/min) | Stirring speed (rpm) | Temperature (° C.) | Duration (h) | kLa (h$^{-1}$) |
|---|---|---|---|---|---|---|
| 1 | 1 | 0 | 0 | 4 | 32 | 0 |
| | 2 | 14.6 | 450 | 31 | 32 | 90 |
| 2 | 3 | 1.46 | 450 | 31 | 32 | ≈10 |
| | 4 | 14.6 | 450 | 31 | 32 | 90 |

TABLE 6-continued

| Week | Run | Aeration Flowrate (L/min) | Stirring speed (rpm) | Temperature (° C.) | Duration (h) | kLa (h$^{-1}$) |
|---|---|---|---|---|---|---|
| 3 | 5 | 14.6 | 50 | 31 | 32 | ≈10 |
| | 6 | 14.6 | 450 | 31 | 32 | 90 |
| 4 | 7 | 14.6 | 450 | 23 | 32 | 90 |
| | 8 | 14.6 | 450 | 31 | 32 | 90 |
| 5 | 9 | 14.6 | 450 | 31 | 3 | 90 |
| | 10 | 14.6 | 450 | 31 | 32 | 90 |

The pre-culture train was prepared as described in Example 1, except that the first and second pre-cultures were prepared in duplicate (2×30 mL first pre-culture: 2×1000 mL second pre-culture). After growth at 35° C. (+/−1° C.) and 150 rpm for 24 h (+/−1 h), the two disposable shake flasks from the second pre-culture were pooled. The pooled pre-culture was used to inoculate a fermenter as soon as the second pre-culture was stopped.

As soon as the pre-defined duration of the conditioning step was reached, conditioning was stopped and the following conditions were used in order to calibrate the 100%-dissolved oxygen (DO) level: temperature (35° C.), head pressure (0.4 bar), air flow rate (14.6 L sparged air per minute) and stirring speed (50 rpm or rotations per minute) before inoculation. 3 mL of an antifoaming agent (Simethicone 15%) are aseptically added in each bioreactor Inoculation was achieved by the addition of 1.5 L of the pooled pre-culture. During the fermentation, the temperature (35° C.) and head pressure (0.4 bar) were maintained at a constant level. Foaming control during the fermentation was performed by addition of antifoam (Simethicone 1.5%). The level of dissolved oxygen was set at 25% and regulated by increasing stirring when the DO fell below 25%. The minimum stirring speed was set at 50 rpm: the maximum stirring speed was set at 1000 rpm. The pH was regulated at 7.2 by addition of acetic acid 50% (w/v or weight/volume).

Experimental Design

The experiment was designed to compare fermentation performance of medium conditioned under optimal process parameters (31° C., 32 h, kLa of 90 h$^{-1}$) with medium conditioned under process parameters differing in only one parameter from optimal.

In week 1, the effect of optimal parameters (Run 2) versus non-conditioned medium (Run 1) was verified. In weeks 2 and 3, effect of low conditioning kLa (Run 3-low aeration and Run 5-low stirring speed) was compared to optimal operating conditions (Runs 4 and 6). In weeks 4 and 5, effect of low temperature (Run 7: 23° C.) and low duration (Run 9: 3 h) were respectively compared to optimum operating parameters (Runs 8 and 10).

Results

Figure 5:
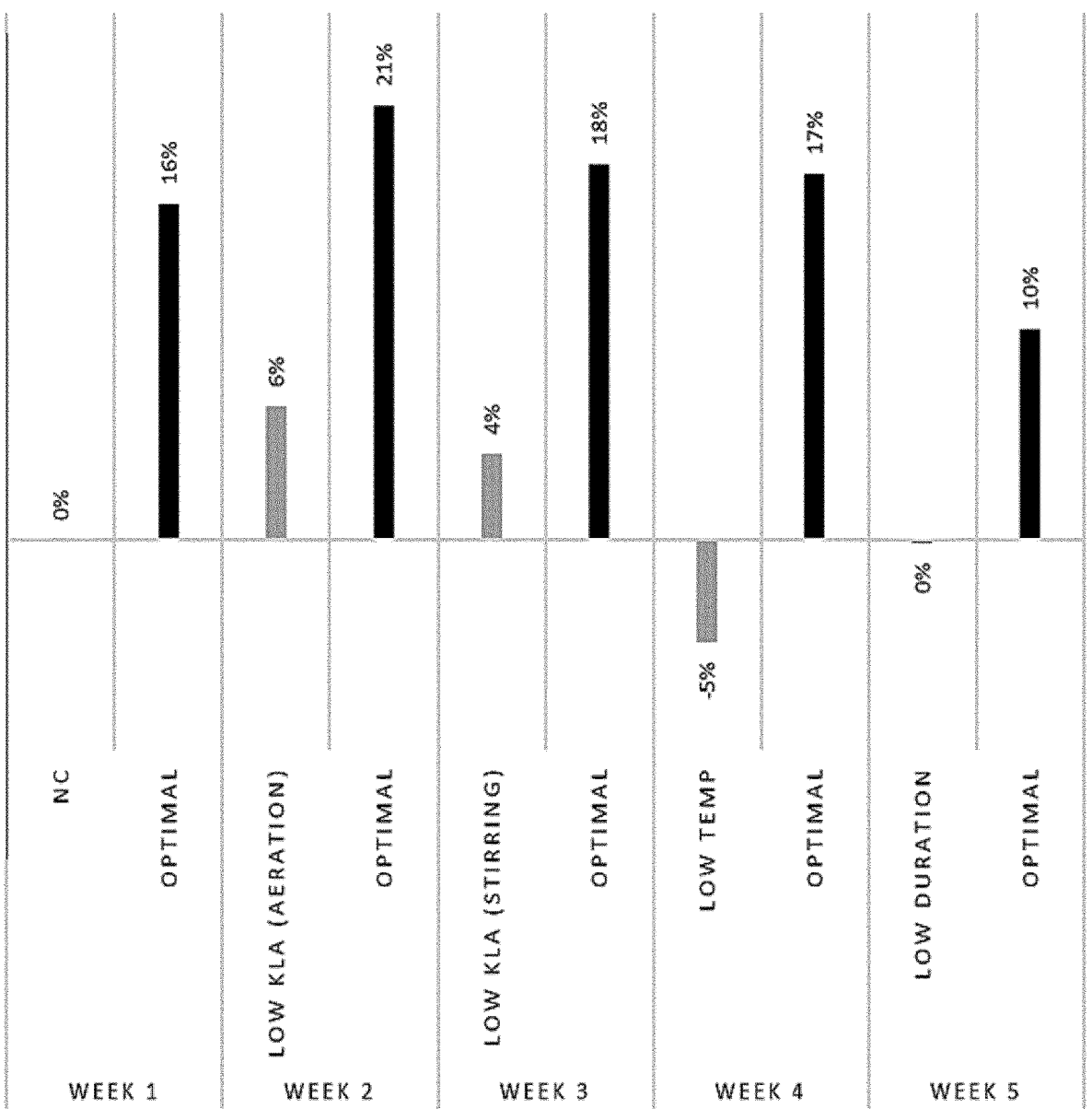
FIG. 5: Validation of optimum conditioning parameters at 20 L bioreactor scale. Fermentation carried out in conditioned medium with optimal process parameters (31° C.: 32 h: kLa 90 h$^{-1}$) produced at least 10% increase in PT yield when compared to non-condition medium (NC) or suboptimal conditioning parameters.

As illustrated in FIG. 5 and Table 7A, fermentation carried out in conditioned medium with optimal process parameters gives a PT yield higher than 10% when compared to:

a non-conditioned medium (week 1)

a medium conditioned with low kLa (~10 h$^{-1}$) resulting of a low aeration flowrate (week 2)

a medium conditioned with low kLa (~10 h$^{-1}$) resulting of a low stirring speed (week 3)

a medium conditioned with a low temperature (23° C.) (week 4)

a medium conditioned with a short duration (3 h) (week 5)

These data confirm optimal operating parameters of medium conditioning for PT yield at 20 L fermentation scale. No negative impacts were observed on biomass yield, FHA yield and fermentation time. Surprisingly, while the small-scale studies described in Examples 1-4 found no effect of low kLa on PT yield, a negative effect of low kLa was observed at 20 L fermentation scale. Thus, duration, temperature and kLa all appear to be important factors to produce the conditioning effect at 20 L fermentation scale.

TABLE 7

Fermentation performances at 20 L scale

| Week | Process parameters | Biomass (OD) | Fermentation time (h) | PT (µg/mL) | FHA (µg/mL) |
|---|---|---|---|---|---|
| | | | Fermentation performance (% change from non-conditioned medium) | | |
| Week 1 | NC | 0% | 0% | 0% | 0% |
| | Optimal | 9% | 1% | 16% | 23% |
| Week 2 | low kLa (aeration) | 13% | −14% | 6% | 21% |
| | Optimal | 14% | −14% | 21% | 23% |
| Week 3 | low kLa (stirring) | 25% | 0% | 4% | −10% |
| | Optimal | 18% | −6% | 18% | 10% |
| Week 4 | low Temp | 19% | −3% | −5% | 12% |
| | Optimal | 18% | −8% | 17% | 12% |
| Week 5 | low duration | 19% | 6% | 0% | 10% |
| | Optimal | 26% | −3% | 10% | −1% |

NC: non-conditioned growth medium

Example 6: Validation of Optimum Conditioning Parameters at Large Scale

Medium conditioning parameters were performed at large scale and validated in *Bordetella* fermentations carried out in small-scale fermentation vessels (<1 L).

Methods

An 800 L fermenter and a 2400 L medium preparation tank were used for large scale medium conditioning prior to inoculation. Sterile growth medium, prepared as in Example 1, was aseptically transferred into the fermenter (800 L) or the medium preparation tank (2400 L) and subjected to the following medium conditioning process parameters (Table 7B). Due to differences between the vessels, such as aeration sparger design and agitation system, the Kla values achieved in the medium preparation tank were lower than those obtained in the fermenter.

TABLE 7

| Run | Sample No. | Aeration Flowrate (L/min) | Stirring speed (rpm) | Temperature (° C.) | Duration (h) |
|---|---|---|---|---|---|
| 1 (800 L fermenter) | 1* | 0 | 0 | 4 | 0 |
| | 2 | 150 | 210 | 35 | 32 |
| 2 (Medium Preparation tank) | 3* | 0 | 0 | 4 | 0 |
| | 4 | 150 | 80 | 35 | 20 |
| | 5 | 150 | 80 | 35 | 32 |

*Non-conditioned growth medium (NC) - Control

Five samples of the sterile conditioned media were collected at different time-points in Novaseptum sampling bags and immediately stored at 4° C.

Each of the five samples was transferred to small-scale fermentation vessel (<1 L) and inoculated with *Bordetella* pre-culture train prepared as described in Example 1, for evaluation of growth and antigen production.

Fermentation performance indicators were assessed by measuring PT and FHA content (ELISA), biomass content (growth curve and final optical density) and fermentation time (measured as described in Example 1).

Results

Figure 6:
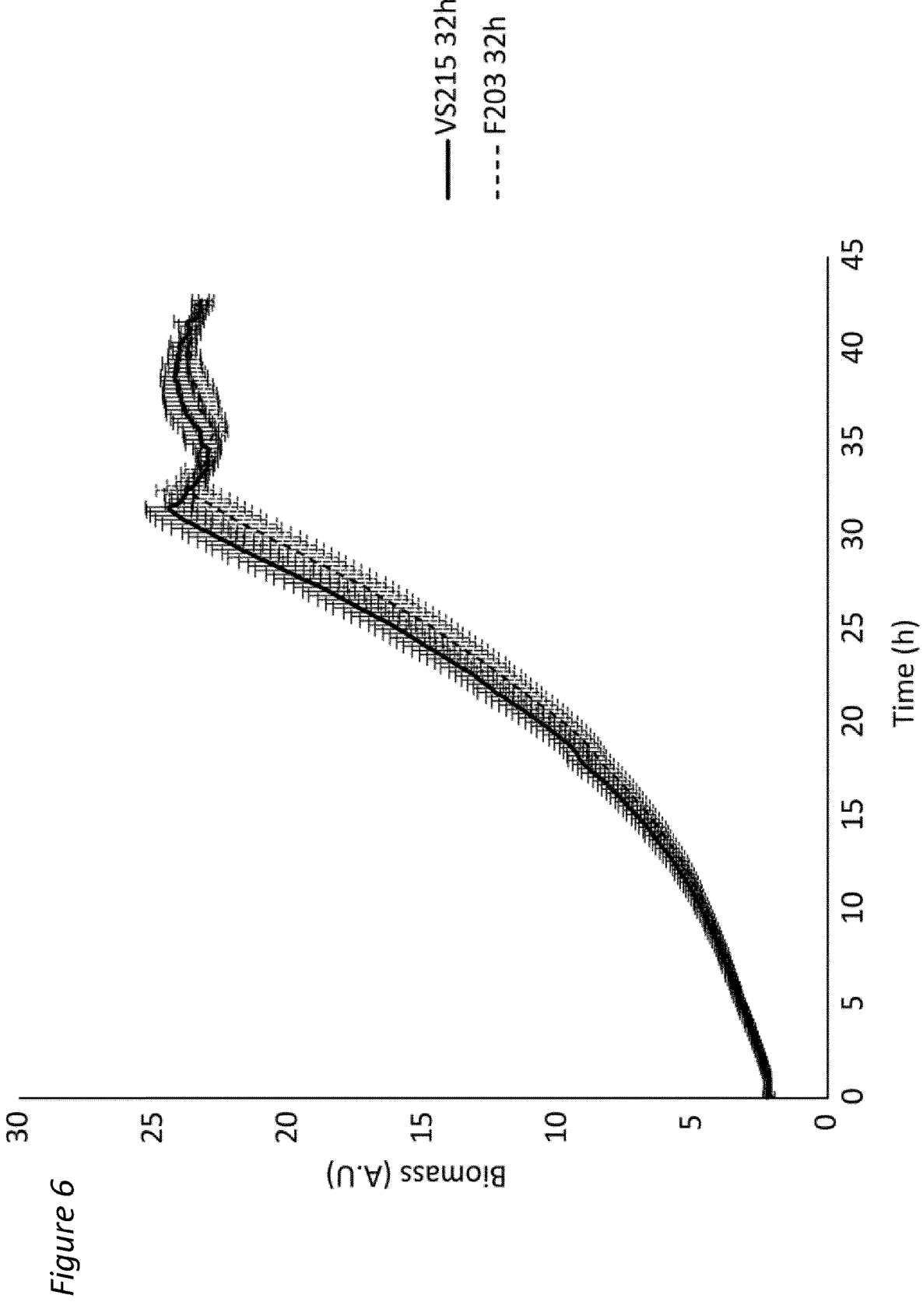
FIG. 6: Average growth curves with error bars (standard deviation) following fermentation in small-scale vessels (<1 L) using medium conditioned in either the 800 L fermentation tank or medium preparation tank.
Figure 7A:
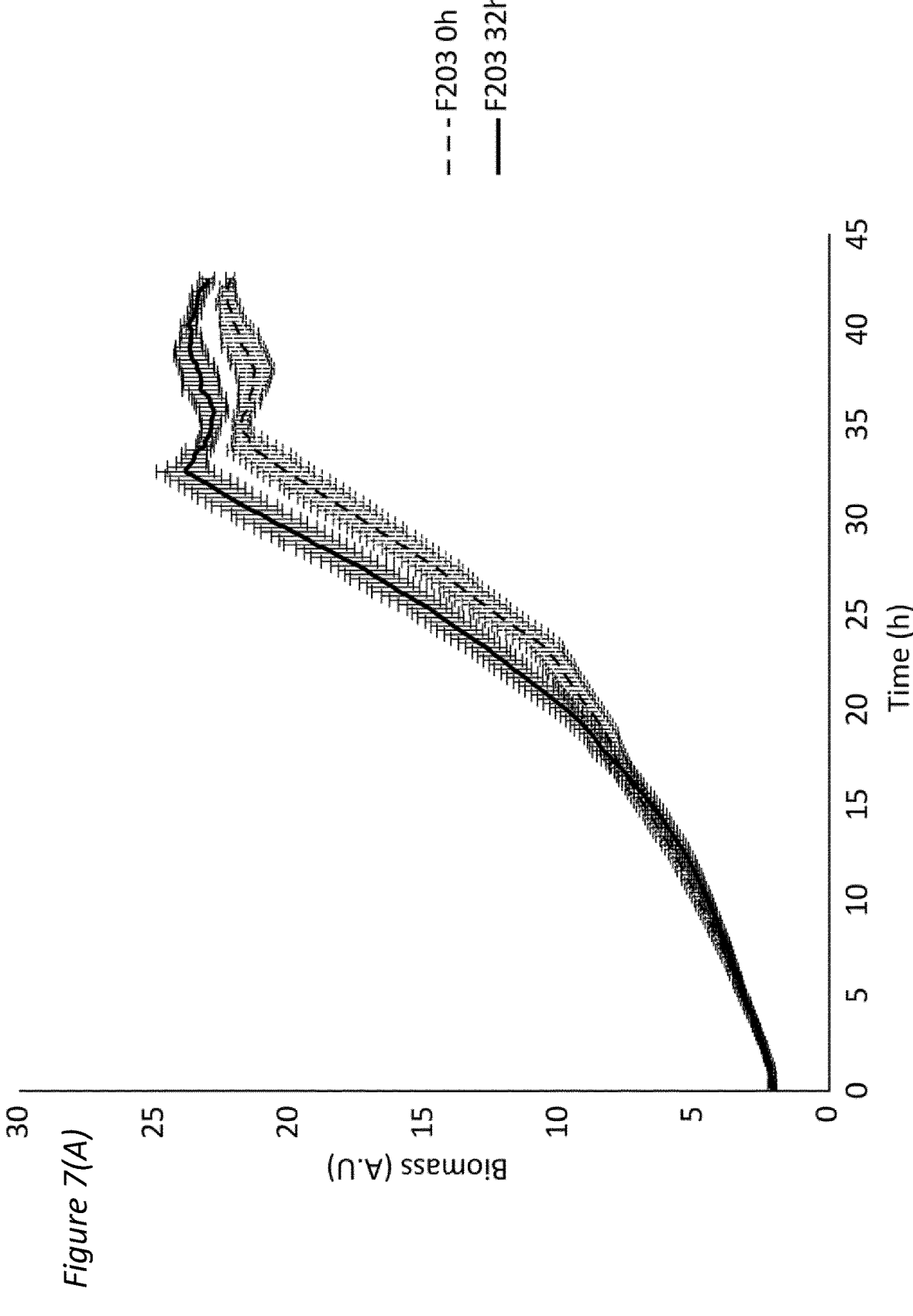
FIG. 7: Average growth curves with error bars (standard deviation) following fermentation in small-scale vessels (<1 L) using (A) medium conditioned for 32 hours in the 800 L fermentation tank versus non-conditioned medium or (B) medium conditioned for 32 hours in the medium preparation tank versus non-conditioned medium.
Figure 7B:
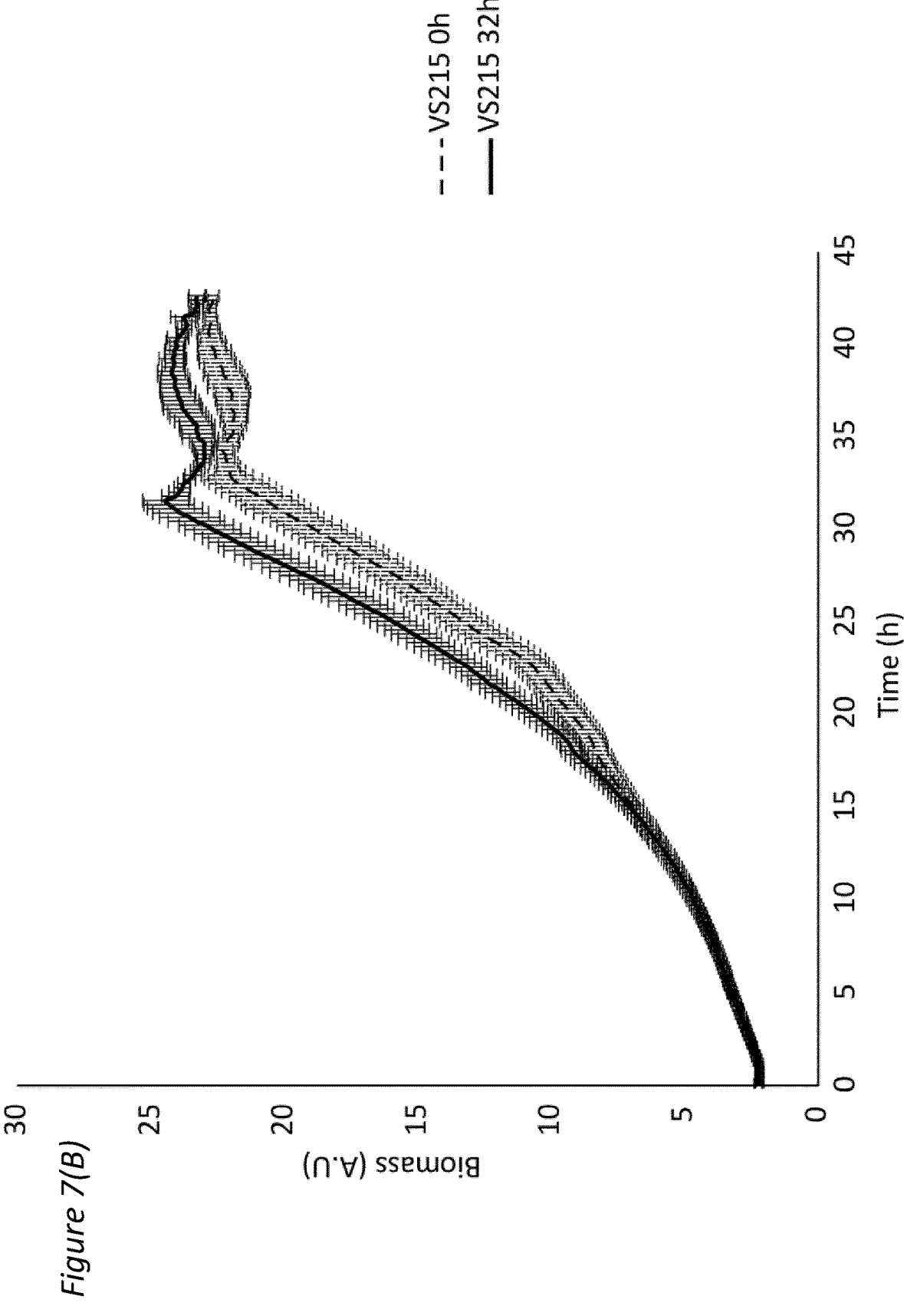

As illustrated in FIG. 6, the effect of medium conditioning on growth performance during subsequent fermentation steps was comparable regardless of the type of vessel used to perform the conditioning step. However, in each case, there was a demonstrable positive effect on fermentation using pre-conditioned medium (FIGS. 7(A) and (B)). "F203" is the medium in the 800 L fermentation tank and "VS215" is the medium in the medium preparation tank.

Figure 8:
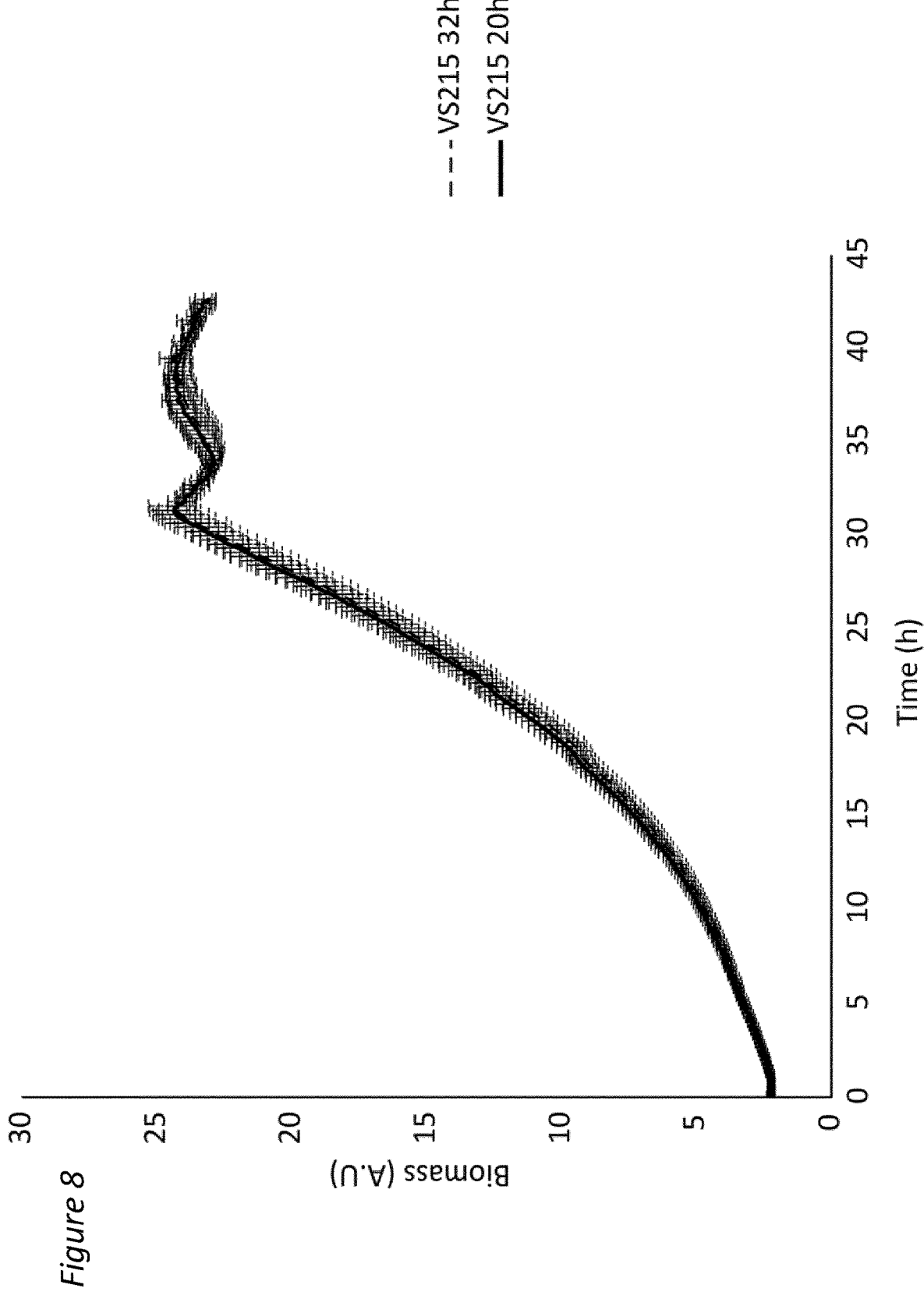
FIG. 8: Average growth curves with error bars (standard deviation) following fermentation small-scale vessels (<1 L) using medium conditioned in the medium preparation tank for either 20 or 32 hours.

In comparison to non-conditioned medium (control), bacterial growth was faster meaning that overall fermentation times could be reduced by around 8% on average. Using conditioned medium, the final biomass achieved was higher than that of the controls (around 9% higher at the start of the stationary phase). Interestingly, the growth performances of media conditioned over 20 hours and 32 hours were comparable (FIG. 8).

Fermentation carried out in conditioned medium improved the yield of both PT and FHA. Specifically, relative to the control, PT productivity increased by 7% after 20 hours of medium conditioning and by 15% after 32 hours of medium conditioning. Similarly, compared to the control, FHA productivity increased by 9% after 20 hours of medium conditioning and by 15% after 32 hours of medium conditioning.

TABLE 8

Summary results of growth performances and antigens productivities. Fermentation time and biomass at start of stationary phase were directly defined from growth curves

| Sample No. | Fermentation time (h) | Biomass (A.U[a]) | Biomass (OD[b]) | PT (µg/mL) | FHA (µg/mL) | PT productivity (µg/mL * h) | FHA Productivity (µg/mL * h) |
|---|---|---|---|---|---|---|---|
| 1 | 35.2 | 21.9 | 4.26 | 4.16 | 190 | 0.118 | 5.4 |
| 2 | 32.5 | 23.6 | 3.64 | 5.02 | 191 | 0.154 | 5.9 |
| 3 | 34.1 | 22.2 | 3.6 | 4.86 | 182 | 0.143 | 5.3 |
| 4 | 31.6 | 24.3 | 3.86 | 4.81 | 183 | 0.152 | 5.8 |
| 5 | 31.6 | 24.3 | 3.80 | 5.19 | 193 | 0.164 | 6.1 |

[a]Value at start of stationary phase, defined from average growth curve;
[b]OD read on samples stored 2 days at 4° C. after end of fermentation These data confirm the positive effects of using a cell-free medium conditioning step at large scale (up to 2400 L) prior to use of the conditioned medium for bacterial fermentation.

We claim:

1. A process for producing a conditioned growth medium for the cultivation of *Bordetella pertussis* species and/or for the production of *Bordetella pertussis* proteins comprising:
   a. providing a sterile growth medium:
   b. holding the sterile growth medium at a temperature between about 28 and about 35° C. for about 20 to 35 hours; and
   c. stirring and/or aerating the sterile growth medium to produce an oxygen volumetric mass transfer coefficient (kLa) of about 10 h$^{-1}$ to about 130 h$^{-1}$, thereby providing the conditioned growth medium for the cultivation of *Bordetella pertussis* species and/or for the production of *Bordetella pertussis* proteins, wherein the growth medium is modified Stainer-Scholte (MSS).

2. The process of claim 1, wherein step b) is carried out at a temperature between about 29° C. and about 33° C., about 30° C. and about 32° C., or about 31° C.; and/or
   wherein step b) is carried out for about 25 to 35 hours, about 30 to 35 hours, or about 32 hours.

3. The process of claim 2, wherein in step c) has at least one of the following conditions,
   the sterile growth medium is stirred continuously for the duration of step b), the stirring is at a stirring speed that produces an oxygen volumetric mass transfer coefficient (kLa) of about 60 h$^{-1}$ to about 130 h$^{-1}$, or about 90 h$^{-1}$; and/or
   the sterile growth medium is aerated continuously for the duration of step b).

4. The process of claim 2, wherein the process is carried out at a scale of at least 10 L, at least 100 L, at least 800 L or at least 1000 L of sterile growth medium.

5. The process of claim 2, wherein, the growth medium further comprises Niacin.

6. The process of claim 1, wherein in step c) has at least one of the following conditions,
   the sterile growth medium is stirred continuously for the duration of step b), the stirring is at a stirring speed that produces an oxygen volumetric mass transfer coefficient (kLa) of about 60 h$^{-1}$ to about 130 h$^{-1}$, or about 90 h$^{-1}$; and/or
   the sterile growth medium is aerated continuously for the duration of step b).

7. The process of claim 6, wherein the process is carried out at a scale of at least 10 L, at least 100 L, at least 800 L or at least 1000 L of sterile growth medium.

8. The process of claim 1, wherein the process is carried out at a scale of at least 10 L, at least 100 L, at least 800 L or at least 1000 L of sterile growth medium.

9. The process of claim 1, wherein the growth medium is modified Stainer-Scholte medium comprising about 1 g/L of dimethyl-B-cyclodextrin and about 10 g/L of acid casein hydrolysate; and/or
   wherein the growth medium is modified Stainer and Scholte medium comprising about 40 mg/L of L-cysteine in place of L-cystine; about 11.84 g/L of Na-L-Glutamate; about 150 mg/L of glutathione; and/or about 400 mg/L of ascorbic acid.

10. A sterile conditioned growth medium produced by the process of claim 1.

11. A process for cultivating a *Bordetella* species comprising:
   a. inoculating the sterile conditioned growth medium of claim 10 with at least one *Bordetella* cell to produce a *Bordetella* culture; and
   b. maintaining the *Bordetella* culture under conditions to allow increase in biomass and/or production of one or more *Bordetella* proteins.

12. The process of claim 11, wherein at least one of the *Bordetella* proteins is selected from the group consisting of pertussis toxin, filamentous haemagglutinin, pertactin and adenylate cyclase.

13. The process of claim 11, wherein the one or more *Bordetella* proteins comprise pertussis toxin which is a genetically detoxified pertussis toxin in which two catalytic residues of the Si subunit (Arg9 and Glu129) are mutated to Lys9 and Gly129; and wherein the one or more *Bordetella* proteins further comprise filamentous haemagluttinin.

14. The process of claim 11, wherein the process further comprises the step of purifying one or more *Bordetella* proteins from the *Bordetella* culture.

15. A process for producing a *Bordetella* protein comprising:
   a. inoculating the sterile conditioned growth medium of claim 10 with at least one *Bordetella* cell to produce a *Bordetella* culture;
   b. maintaining the *Bordetella* culture under conditions to allow production of at least one *Bordetella* protein; and
   c. isolating said at least one *Bordetella* protein from the culture.

* * * * *